(12) United States Patent
Sun et al.

(10) Patent No.: US 9,895,229 B2
(45) Date of Patent: Feb. 20, 2018

(54) METHOD FOR MANUFACTURING IMPLANT HAVING POROUS LAYER ON SURFACE THEREOF

(71) Applicant: CORENTEC CO., LTD., Chungcheongnam-do (KR)

(72) Inventors: Doo-Hoon Sun, Seoul (KR); Yong-Sik Kim, Seoul (KR); Jung-Sung Kim, Chungcheongnam-do (KR); Tae-Jin Shin, Chungcheongnam-do (KR); Byung-Soo Kim, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 1 day.

(21) Appl. No.: 14/831,159

(22) Filed: Aug. 20, 2015

(65) Prior Publication Data

US 2015/0351913 A1    Dec. 10, 2015

Related U.S. Application Data

(63) Continuation-in-part of application No. 13/997,537, filed as application No. PCT/KR2011/008508 on Nov. 9, 2011, now abandoned.

(30) Foreign Application Priority Data

Jan. 4, 2011    (KR) ........................ 10-2011-0000439

(51) Int. Cl.
*A61F 2/30* (2006.01)
*A61F 2/32* (2006.01)
*A61F 2/38* (2006.01)

(52) U.S. Cl.
CPC ........ *A61F 2/3094* (2013.01); *A61F 2/30767* (2013.01); *A61F 2/32* (2013.01);
(Continued)

(58) Field of Classification Search
CPC ...... B22F 3/1055; B33Y 10/00; A61F 2/3094; A61F 2/30767
(Continued)

(56) References Cited

U.S. PATENT DOCUMENTS

| | | | |
|---|---|---|---|
| 7,241,313 B2 | 7/2007 | Unwin et al. | |
| 2007/0142914 A1* | 6/2007 | Jones | A61F 2/30907 623/14.13 |

(Continued)

FOREIGN PATENT DOCUMENTS

| | | |
|---|---|---|
| KR | 10-2002-0070685 | 9/2002 |
| KR | 10-2008-0017665 | 2/2008 |
| KR | 10-2010-0013016 | 2/2010 |

OTHER PUBLICATIONS

International Search Report and Written Opinion dated Jul. 20, 2012, issued in PCT application No. PCT/KR2011/008508, filed Nov. 9, 2011.

*Primary Examiner* — Weiping Zhu
(74) *Attorney, Agent, or Firm* — Workman Nydegger

(57) ABSTRACT

Disclosed herein is a method for manufacturing an implant that is to be surgically inserted in vivo, such as in an artificial knee or artificial hip. According to the method, the porous layer contains pores that have a vertically curved shape with a radius of 100 to 300 μm, thus allowing a bond to grow into the pores to enhance bond adhesion, and an interconnection space is formed between turning points in adjacent unit base layers to increase the ratio of interconnection between pores, whereby bones are allowed to grow into the pores to increase bone adhesion.

26 Claims, 20 Drawing Sheets

(52) U.S. Cl.
CPC ......... *A61F 2/38* (2013.01); *A61F 2002/3093* (2013.01); *A61F 2002/3097* (2013.01); *A61F 2002/30769* (2013.01); *A61F 2310/00023* (2013.01); *A61F 2310/00029* (2013.01)

(58) Field of Classification Search
USPC ..................................................... 623/23.53
See application file for complete search history.

(56) References Cited

U.S. PATENT DOCUMENTS

| | | |
|---|---|---|
| 2007/0282432 A1 | 12/2007 | Stinson et al. |
| 2008/0131479 A1* | 6/2008 | Weber ...................... A61F 2/82 424/426 |
| 2010/0137997 A1 | 6/2010 | Casari et al. |

* cited by examiner specimen ①
sample holder ②
eye hook ③ specimen　①
sample holder　②
cardan shaft　③

① Controll panel
② Specimen tested
③ Abrading wheel
④ Vacuum Pick-up Nozzel

METHOD FOR MANUFACTURING IMPLANT HAVING POROUS LAYER ON SURFACE THEREOF

CROSS-REFERENCE TO RELATED APPLICATIONS

This application is a continuation-in-part of U.S. application Ser. No. 13/997,537, filed Jun. 24, 2013, which is a nationalization of PCT Application No. PCT/KR11/08508, filed Nov. 9, 2011, which claims priority to Korean Application No. 10-2011-0000439, filed Jan. 4, 2011, which applications are incorporated herein by specific reference.

BACKGROUND OF THE INVENTION

1. Field of the Invention

The present invention relates to a method for manufacturing an implant that is to be surgically inserted in vivo, such as in an artificial knee or artificial hip. More particularly, the present invention relates to a method for manufacturing an implant for in vivo insertion, wherein the bone adhesion of the implant into pores, the adhesivity between the implant and the porous coating layer, and the adhesivity between particles in the porous coating layer can be increased by increasing the porosity of the porous coating layer, and wherein the rate of interconnection between pores in the porous coating layer is increased, whereby bones growing into the pores are interconnected, thereby increasing the adhesivity between the implant and the bones.

2. Description of the Related Art

An implant for in vivo insertion refers commonly to a medical component that is surgically inserted into the body. Examples of implants may include: a thighbone bonding member and a shinbone bonding member, which are surgically inserted into a thighbone region and a shinbone region, respectively, for the purpose of artificial knee joint surgery; and a hipbone cup and a thigh stem, which are surgically inserted into a hipbone region and a thighbone region, respectively, for the purpose of artificial hip joint surgery.

Of implants for in vivo insertion, an artificial hip joint, as shown in FIG. 1, includes a hipbone cup 113 fixed in a hipbone of the pelvis 114, and a thigh stem 111 inserted and fixed in a thighbone 112. The thigh stem 111 and the hipbone cup 113 are made of a titanium alloy or the like, which is harmless to the human body. At an end of the thigh stem 111, a thighbone head 115 made of ceramic or a metal material is fixed, while the hipbone cup 113 is provided therein with a hemispherical seal 116 in which the thighbone head 115 is rotatable. The hemispherical seal 116 is made of a ceramic material or polyethylene. Such an artificial hip joint is configured such that the thighbone head 115 can be rotated on the hemispherical seal 116 as the thighbone 112 and the thigh stem 111 move. Turning to the artificial knee joint, its structure is shown in FIG. 1. In the artificial knee joint, as shown, a thighbone bonding member 117 is fixed at a shinbone bone-facing end of the thighbone 8, and a shinbone bonding member 119 is fixed at a thighbone-facing end of the shinbone 120, so that the thighbone bonding member 117 can be rotated with regard to the shinbone bonding member 119.

Typical among raw materials of implants such as the thigh stem 111, the hipbone cup 113, the thighbone bonding member 117 and the shinbone bonding member 119 are titanium, titanium alloys, and cobalt-chromium alloys. Particularly, titanium and titanium alloys are most widely used, not only because they are easy to process, but also because they are suitable for use as biomaterials thanks to their superiority in biological affinity, mechanical strength and corrosion resistance. However, an implant made of titanium, a titanium alloy or a chromium-cobalt alloy alone is unlikely to be successfully implanted because it takes a long time for the implant to initially bond with bones after implantation into the body.

In order to solve this problem, a method has been proposed for forming a porous coating layer on the surface of an implant made of only titanium, a titanium alloy or a chromium-cobalt alloy. However, conventional porous coating layers formed thus far suffer from the following problems: it is difficult to increase the number of pores in the porous coating layer formed on the surface of the implant and thus the porosity of the porous coating layer (as a rule, bone adhesion increases with porosity since bones grow into the pores and bind to the implant); when the porosity of the porous coating layer is artificially increased, the adhesion strength between the porous coating layer and the implant (matrix material) and the inter-crystalline adhesion of the porous coating layer are weakened, causing the coating layer to readily separate from the surface of the implant due to friction upon implantation, and the separated porous coating layer inhibits the growth of the bone into the implant, resulting in a reduced stress dissipation effect and preventing the implant from being strongly fixed in the bone.

In addition, the interconnection of pores in the coating layer, that is, the formation of paths, is needed to connect the bones growing into the pores, thus increasing bone adhesion. However, it is difficult to form a coating layer that allows for the interconnection of pores.

Moreover, curved pores in such a coating layer can further increase bone adhesion. However, it is also difficult to form a porous coating layer provided therein with precisely controlled curved pores.

SUMMARY OF THE INVENTION

Accordingly, the present invention has been devised to solve the above-mentioned problems, and an object of the present invention is to provide a method for manufacturing an implant for in vivo insertion, with a porous layer formed on the surface thereof, by which the porous layer formed on the surface of the implant has enhanced porosity, with the aim of increasing bone adhesion into pores, and reinforcing the bonding strength between the implant and the porous layer and between particles within the porous layer.

Another object of the present invention is to provide a method for manufacturing an implant for in vivo insertion, with a porous layer formed on the surface thereof, in which the implant is melted together with metal powder to form a porous layer that has no boundaries with the matrix material of the implant, but is integrated into the implant, whereby the binding strength between the porous layer and the matrix material can be increased.

Another object of the present invention is to provide a method for manufacturing an implant for in vivo insertion, with a porous layer formed on the surface thereof, in which the porous layer contains pores that have a vertically curved shape with a radius of 100 to 300 µm, thus allowing a bond to grow into the pores to enhance bond adhesion.

Another object of the present invention is to provide a method for manufacturing an implant for in vivo insertion, with a porous layer formed on the surface thereof, in which an interconnection space is formed between turning points in adjacent unit base layers to increase the ratio of interconnection between pores, whereby bones are allowed to grow into the pores to increase bone adhesion.

Another object of the present invention is to provide a method for manufacturing an implant for in vivo insertion, with a porous layer formed on the surface thereof, in which the amount of metal powder sprayed over the implant varies depending on a path, so that a unit base layer and a unit additional layer vary in shape depending on the path, whereby binding strength between the bone and the implant can be increased.

Another object of the present invention is to provide a method for manufacturing an implant for in vivo insertion, with a porous layer formed on the surface thereof, in which the intensity and time of laser beam irradiation for melting metal powder are adjusted to allow a unit base layer and a unit additional layer to be shaped differently depending on a path, whereby the binding strength between the bone and the implant can be increased.

Another object of the present invention is to provide a method for manufacturing an implant for in vivo insertion, with a porous layer formed on the surface thereof, in which a washing step for removing metal powder is carried out to increase the porosity of a unit base layer and a unit additional layer.

Another object of the present invention is to provide a method for manufacturing an implant for in vivo insertion, with a porous layer formed on the surface thereof, in which part of an additional layer is deposited on a base layer and the remainder is formed on the surface of the implant, thereby increasing the porosity and roughness of the porous layer.

In order to accomplish above objects, an aspect of the present invention provides a method for manufacturing an implant for in vivo insertion, the implant having a porous layer formed on a surface thereof, the method comprising a base layer forming step for forming a base layer integrated into a matrix material surface of the implant, the base layer forming step including:
- a unit base layer forming step for completing a unit base layer by conducting:
- a first molten paste forming step in which a laser beam is radiated into the matrix material surface to locally form a molten paste,
- a first metal powder spraying step in which a metal powder uniform in size is sprayed over the molten paste, and
- a first wall forming step in which the first molten paste forming step and the first metal powder spraying step are carried out along a predetermined path to form a wall having a predetermined pattern/thickness/width; and
- a base layer completing step for completing a base layer composed of multiple unit base layers by repeating the unit base layer forming step.

According to one embodiment, the base layer formed in the base layer completing step has a predetermined gap between two adjacent unit base layers.

According to another embodiment, the gap between the unit base layers formed in the base layer completing step is wide so that a turning point of one of the multiple unit base layers is not in contact with that of a remaining one of the multiple unit base layers, whereby an interconnecting space is formed through which pores in the multiple unit base layers communicate with one another.

According to another embodiment, the predetermined path along which the first molten paste forming step and the first metal powder spraying step are carried out in the first wall forming step is composed of a plurality of identical unit base layer paths.

According to another embodiment, the metal powder is sprayed in non-uniform amounts per unit area over the molten paste at individual turning points in the first wall forming step.

According to another embodiment, an amount of the metal powder, sprayed over the molten paste, that is molten is controlled by adjusting laser beam irradiation in intensity and/or time per unit area on the path in the first wall forming step when the implant is locally melted on the surface thereof.

According to another embodiment, the method further comprises an additional layer forming step for forming an additional layer on the implant in which the base layer is formed, the additional layer forming step including:
- a unit additional layer forming step for completing an unit additional layer by conducting:
- a second molten paste forming step in which a laser beam is radiated to an upper surface of the unit base layer and a surface of the implant to locally form a molten paste;
- a second metal powder spraying step in which metal powder with a predetermined size is sprayed to the molten paste in the second metal powder spraying step;
- a second wall forming step in which the second molten paste forming step and the second metal powder spraying step are carried out along a predetermined path to form a wall having a predetermined pattern/thickness/width; and
- an additional layer completing step for completing an additional layer composed of multiple unit additional base layers by repeating the unit base layer forming step.

According to another embodiment, the additional layer formed in the additional layer completing step has a predetermined gap between two adjacent ones of the unit additional layers.

According to another embodiment, the gap between the unit additional layers formed in the additional layer completing step is wide so that a turning point of one unit additional layer is not in contact with that of the other.

According to another embodiment, the metal powder is sprayed in non-uniform amounts per unit area over the molten paste formed on the upper surface of the base layer and the surface of the implant at individual turning points in the second wall forming step.

According to another embodiment, the predetermined path along which the second molten paste forming step and the second metal powder spraying step are carried out in the second wall forming step is composed of a plurality of identical unit additional layer paths.

According to another embodiment, a molten amount of the metal powder sprayed over the molten paste is controlled by adjusting laser beam irradiation in intensity and/or time per unit area on the path in the first wall forming step when the upper surface of the base layer and the surface of the implant are locally melted.

According to another embodiment, the porous layer formed on the surface of the implant and/or the upper surface of the base layer has contains pores that are vertically curved, with a radius of 100~300 μm, whereby the pores allow the bone to grow thereinto, thus increasing adhesivity between the bone and the implant.

According to another embodiment, the unit base layers or unit additional layers have protrusions wherein adjacent protrusions are connected to form a bridge beneath which a void exists, allowing a bone to grow therein, so that the pores are interconnected to enhance bone adhesion.

According to another embodiment, the tool that radiates the laser beam and sprays metal powder is set to move at a speed of 0.6~2.3 m/min with a movement interval of 0.5~1.0 mm and to produce the laser beam at an intensity of 90~1000 W in the base forming step and the additional layer forming step so that the porous layer formed on the surface of the implant has a thickness of 200~1000 μm, a pore size of 150~800 μm, a porosity of 40~70 vol %, and a roughness of 100 μm or higher.

According to another embodiment, the spraying of the metal powder and the radiation of the laser beam in the first metal powder spraying step and the first molten paste forming step are repeatedly conducted along a unit base layer path set to be a 'right-forward-left-forward' directional pattern.

According to another embodiment, the spraying of the metal powder and the irradiation of the laser beam in the second metal powder spraying step and the second molten paste forming step are repeatedly conducted along a unit additional layer path set to be a 'left-forward-right-forward' directional pattern symmetric to the unit base layer path with regard to a central line of the unit base layer.

According to another embodiment, the metal powder sprayed to the surface of the implant in the first metal powder spraying step has a size of 40~150 μm.

According to another embodiment, the metal powder sprayed to the surface of the implant in the second metal powder spraying step has a size of 40~150 μm.

According to another embodiment, the method further comprises a washing step in which metal powder remaining in a non-molten state upon the formation of the base layer or the additional layer is removed by washing after the completion of the additional layer.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE REFERENCE NUMERALS IN THE DRAWINGS

Figure 1:
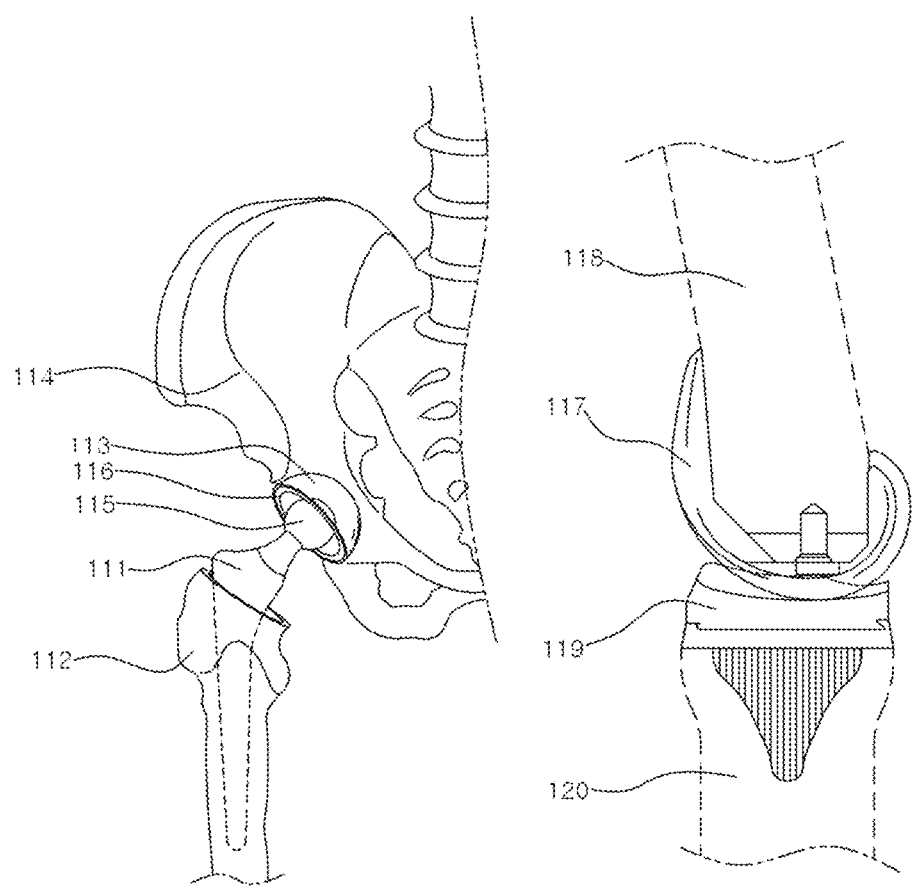
FIG. 1 is a reference view showing an artificial hip joint and an artificial knee joint as examples of implants.

1: implant
3: porous layer
31: base layer 311: unit base layer 311a: $1^{st}$ wall
33: additional layer
331: unit additional layer 331a: $2^{nd}$ wall
S1: base forming step
S11: unit base layer forming step
S111: $1^{st}$ molten paste forming step
S113: $1^{st}$ metal powder spraying step
S115: $1^{st}$ wall forming step
S13: base layer completing step
S3: additional layer forming step
S31: unit additional layer forming step
S311: $2^{nd}$ molten paste forming step
S313: $2^{nd}$ metal powder spraying step
S315: $2^{nd}$ wall forming step
S33: additional layer completing step
S5: washing step
a: pore b: tool movement interval
c: turning point d: interconnection space
e1: unit base layer path
e2: unit additional layer path
f: protrusion g: depression h: bridge

DESCRIPTION OF THE PREFERRED EMBODIMENTS

Reference now should be made to the drawings, throughout which the same reference numerals are used to designate the same or similar components. Unless defined otherwise, all technical and scientific terms used herein have the same meanings as commonly understood by one of ordinary skill in the art. Throughout the accompanying drawings, the same reference numerals are used to designate the same or similar components. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, description thereof will be omitted.

First, a description is given of a rapid metal prototyping technique for use in forming a porous coating layer, and then of a method for forming an amorphous porous layer on the surface of an implant for in vivo insertion according to the present invention.

Rapid prototyping technology is a new-concept rapid prototyping technology of directly manufacturing a three-dimensional product or manufacturing a tool necessary for the three-dimensional product in a very short period of time using geometric data (three-dimensional CAD data, CT data, MRI data, digital data measured as three-dimensional data, etc.) stored in a computer. Rapid metal prototyping technology allows complicated final products and various kinds of tools to be manufactured more rapidly than cutting, casting or the like using CNC (computer numerical control) and other working machines. The term "rapid metal prototyping technology" as used herein, is intended to encompass SLS (Selective Laser Sintering), DMLS (Direct Metal Laser Sintering), SLM (Selective Laser Melting), EBM (Electron Beam Melting), DMT (laser-aided Direct Metal Tooling), LENS (Laser-Engineered Net Shaping), DMD (Direct Metal Deposition), DMF (Direct Metal Fab) and the like.

Figure 2:
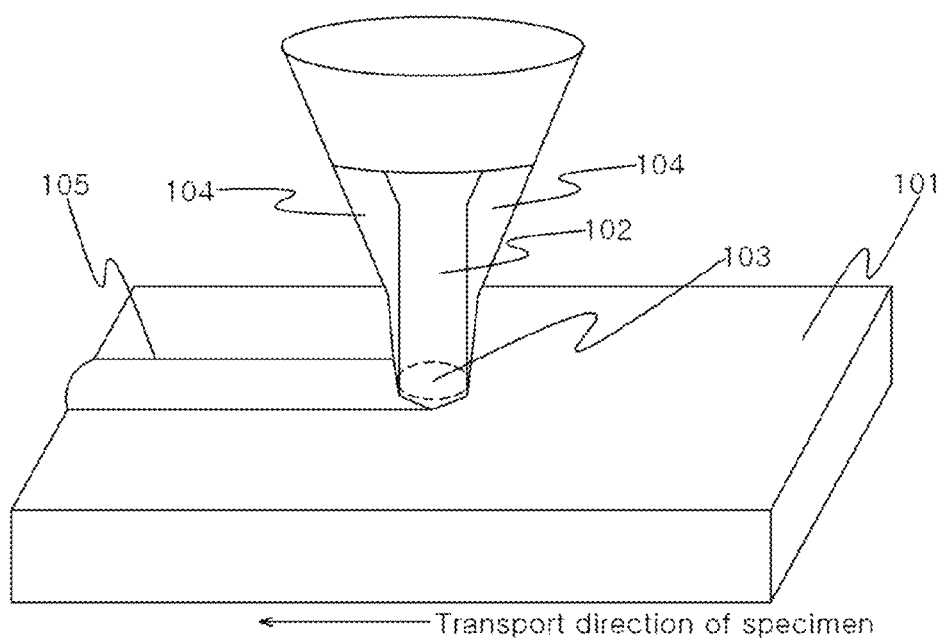
FIG. 2 is a view explaining a rapid metal prototyping technology.

An example of the application of rapid metal prototyping technology is illustrated in FIG. 2. As shown in FIG. 2, the surface of a sample 101 is irradiated with a laser beam 102 to convert part of it into molten paste 103 while a powdered cladding material 104 (e.g., a metal, a metal alloy or the like) is supplied to the molten paste to form a new cladding layer 105 on the surface of the sample 101. Rapid metal prototyping technology is designed to compute two-dimensional section information from three-dimensional CAD data, and to sequentially form cladding layers having shapes, thicknesses and/or heights corresponding to the two-dimensional section information, thus rapidly forming a three-dimensional functional metal product or a tool.

In this regard, the shape and height of the cladding layer is precisely set by controlling a tool course computed from two-dimensional section information and processing variables such as laser output, the mode and intensity of the laser beam, the moving speed of a sample, the characteristics of cladding powder, the amount of cladding powder that is supplied, the speed at which cladding powder falls and the like. The present invention, therefore, takes advantage of rapid metal prototyping technology to obtain data on a porous coating layer of interest, such as data on height, pore size, pore shape, porosity, etc., and to use the data in forming the porous coating layer, thereby increasing bone adhesion and the adhesive strength of the thigh stem to bone.

Figure 3:
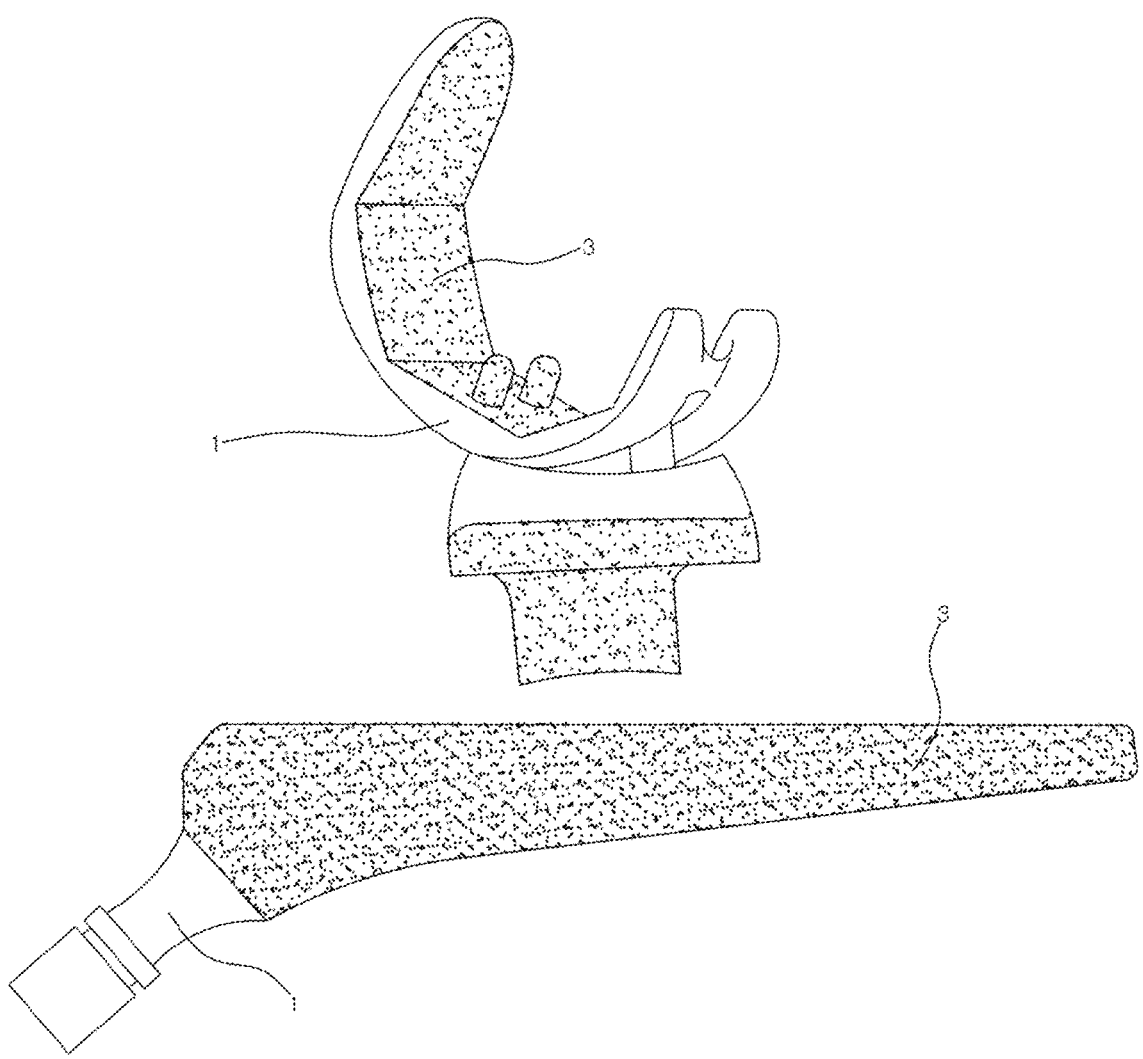
FIG. 3 is a perspective view showing implants (artificial hip joint and artificial knee joint) for in vivo insertion manufactured by a method for manufacturing an implant having a porous layer formed on a surface thereof in accordance with the present invention.

A method for manufacturing an implant having a porous layer on the surface thereof (in FIG. 3, an artificial knee joint and a thigh stem for an artificial hip joint are shown as examples of the implant) is characterized in that metal powder is melted and applied to the surface of the implant 1 to form a porous coating layer 3, 200-1000 μm thick, with 150-800 μm-size pores formed at a porosity of 40-70 vol. % in the porous layer, whereby the porous layer 3 can be imparted with high porosity and bond strength between the implant 1 and the porous layer and between metal powders in the porous layer.

The implant 1 is made of titanium, a titanium alloy, a cobalt-chrome alloy or a stainless steel alloy, which are generally used as biocompatible materials because they have excellent bioaffinity, mechanical strength and corrosion resistance. With the aim of increasing the success rate at which the implant 1 is transplanted into the human body by decreasing the initial bonding time of the implant 1 and bone, a porous coating layer 3 is formed on the surface of the implant 1.

The porous coating layer 3 is configured such that pores (a) are formed in the surface of the implant 1 using biocompatible material powder such as titanium powder, titanium alloy powder, cobalt-chromium alloy powder or the like, with the aim of increasing the adhesivity between the implant 1 and bone when the bone has grown into the pores after the transplantation of the implant 1 into the human body. Conventionally, attempts have been made to form a pore-bearing coating layer on the surface of an implant 1. However, conventional porous coating layers formed thus far suffer from the following problems: it is difficult to increase the number of pores in the porous coating layer formed on the surface of the implant and thus the porosity of the porous coating layer (as a rule, bone adhesion increases with porosity since bones grow into the pores and bind to the implant); when the porosity of the porous coating layer is artificially increased, the strength of adhesion between the porous coating layer and the implant 1 (matrix material) and the inter-crystalline adhesion of the porous coating layer are weakened, causing the coating layer to readily separate from the surface of the implant 1 due to friction upon implantation; and the separated porous coating layer inhibits the growth of the implant 1 into the bone, resulting in a reduced stress dissipation effect and preventing the implant from being strongly fixed in the bone. In the present invention, as described above, the porosity, as well as the height of the porous coating layer 3 and the size and shape of the pores therein are obtained using the above-mentioned laser processing conditions and/or metal powder spraying paths, and are used to enhance bone adhesion and to increase the adhesivity between the thigh stem and the bone and between particles in the porous coating layer 3.

Figure 4:
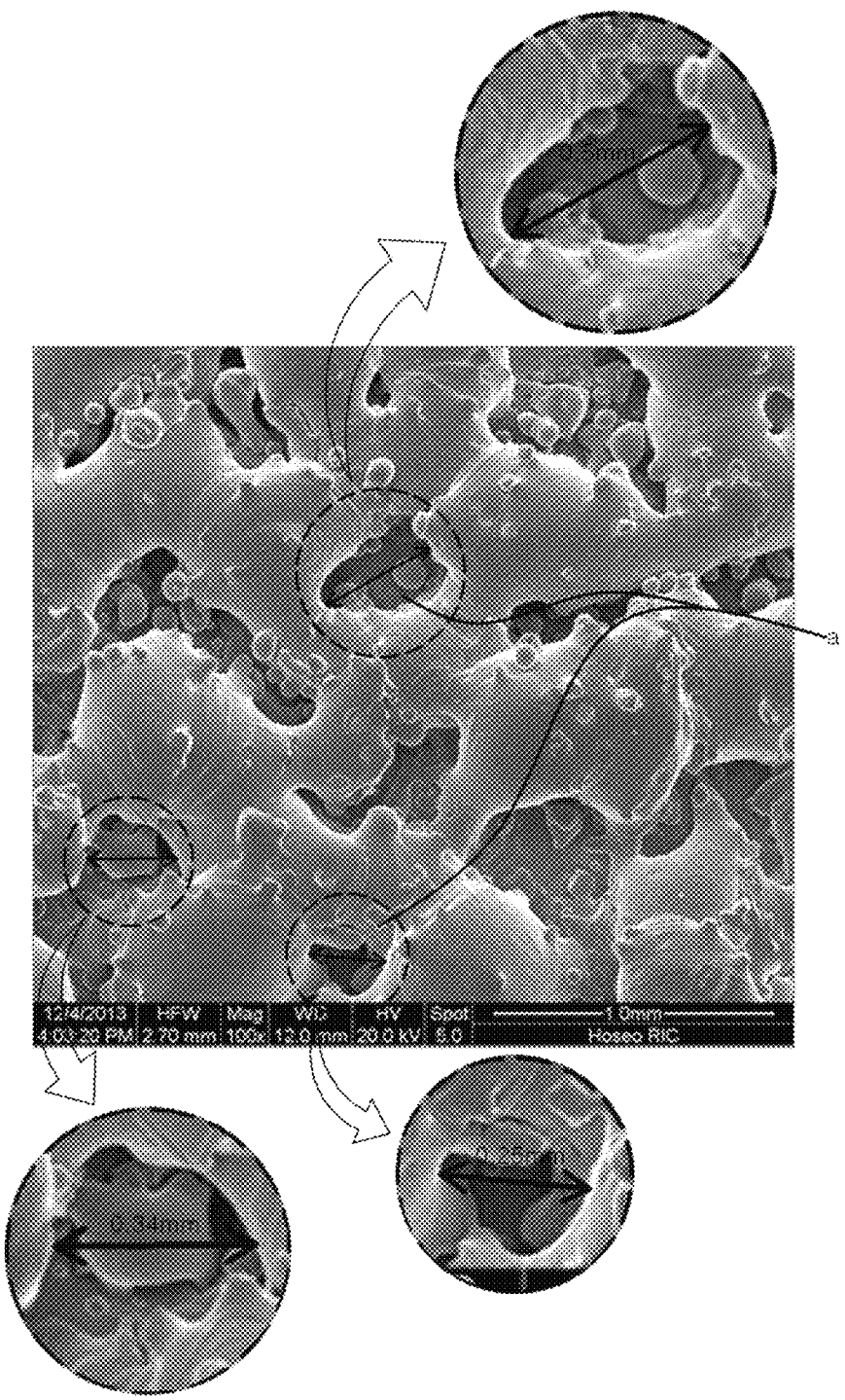
FIG. 4 is an electron microscope image showing the pore size of the porous layer of FIG. 3.
Figure 5:
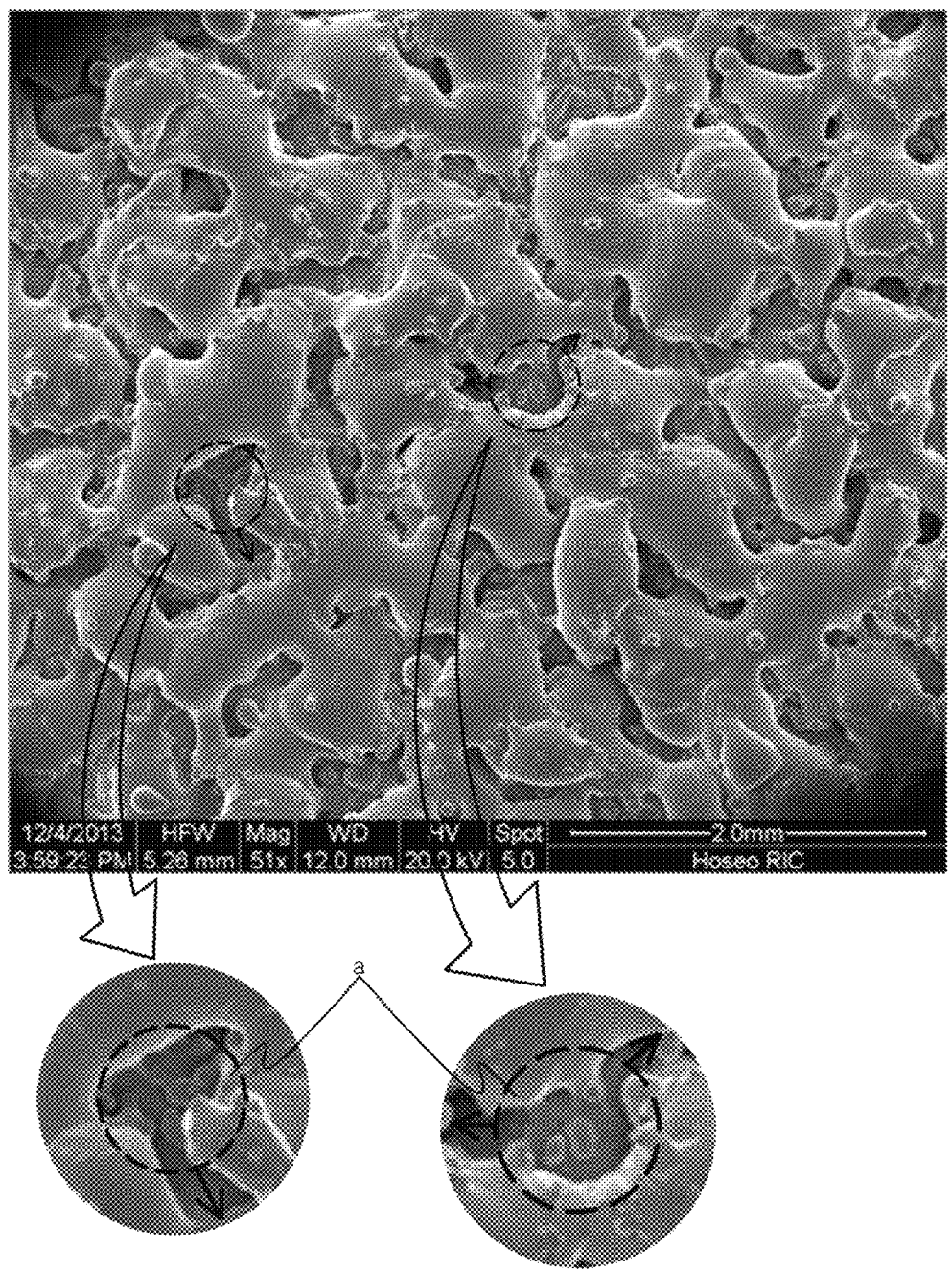
FIGS. 5 and 6 are electron microscope image showing the connection state of pores of the porous layer of FIG. 3.
Figure 6:
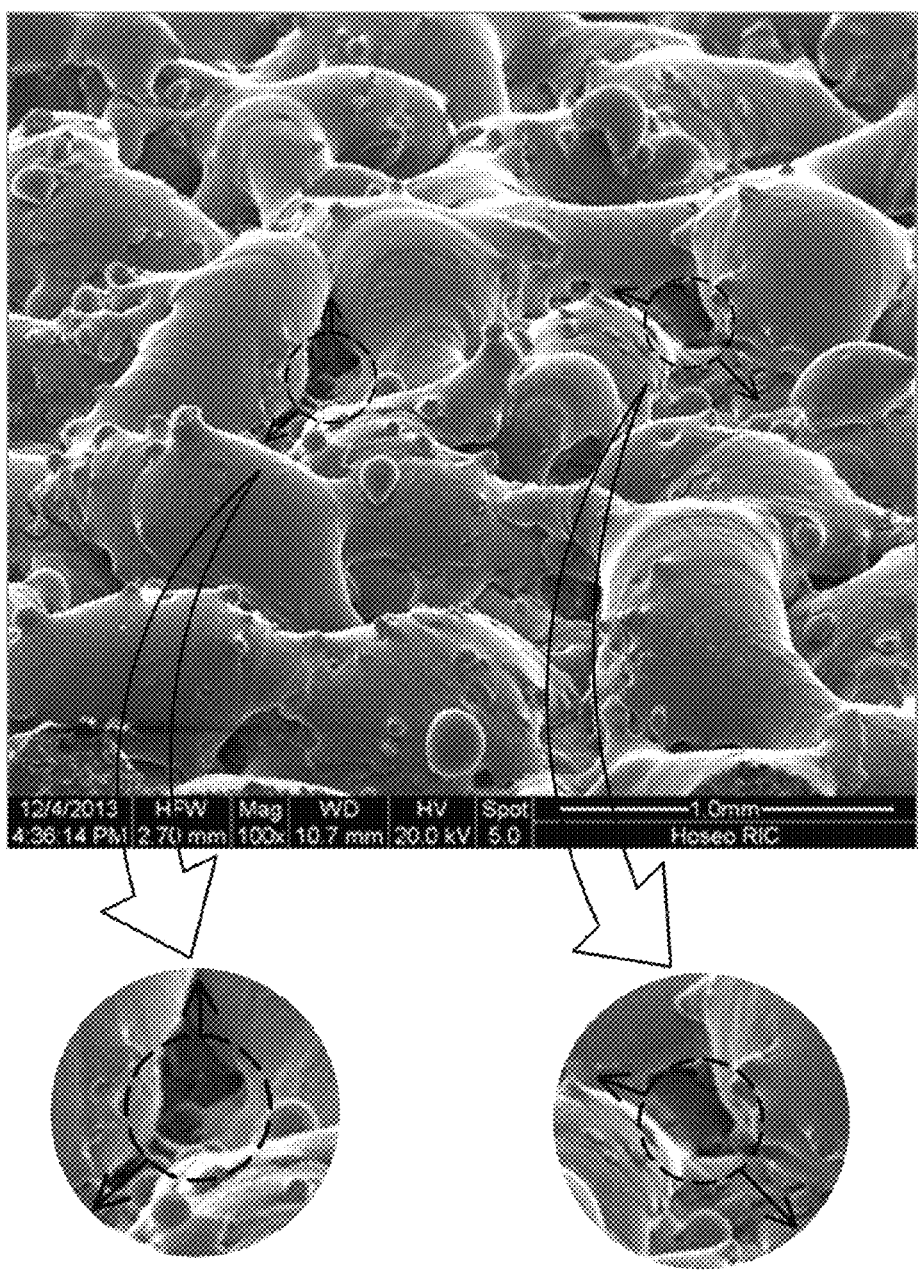

Particularly, the implant 1 of the present invention is characterized in that the porous coating layer 3 has a thickness of 200-1,000 μm, with pores 150-800 μm in size formed at a porosity of 40-70 vol % and at a roughness of 100 μm therein (refer to FIG. 4), whereby the porous layer 3 can be imparted with high porosity and bond strength between the implant 1 and the porous layer and between the metal powders in the porous layer. In order to increase only the adhesion of the implant 1 to the bone, that is, bone adhesion, by growing the bone into the porous layer formed on the implant 1, it is advantageous to increase the porosity of the porous layer 3. In this regard, however, the adhesive strength between the porous layer 3 and the matrix material of the implant, as well as the adhesivity between particles within the porous layer 3, is reduced, which causes the porous layer 3 to readily separate from the surface of the implant 1 due to friction upon implantation. The separated porous layer 3 inhibits the growth of the implant 1 into the bone, resulting in a reduced stress dissipation effect and preventing the implant 1 from being strongly fixed in the bone. In the present invention, hence, the porous layer 3 is formed at the thickness mentioned above, with pores (a) of the size formed at a relatively high porosity of 40-70 vol % therein, whereby the adhesive strength between the porous layer 3 and the matrix material of the implant 1, as well as the adhesivity between particles within the porous layer 3, can be maintained at a desirable level (as will later be demonstrated with reference to test data). For this, the porous layer 3 may include a base layer 31 and an additional layer 33.

Figure 7:
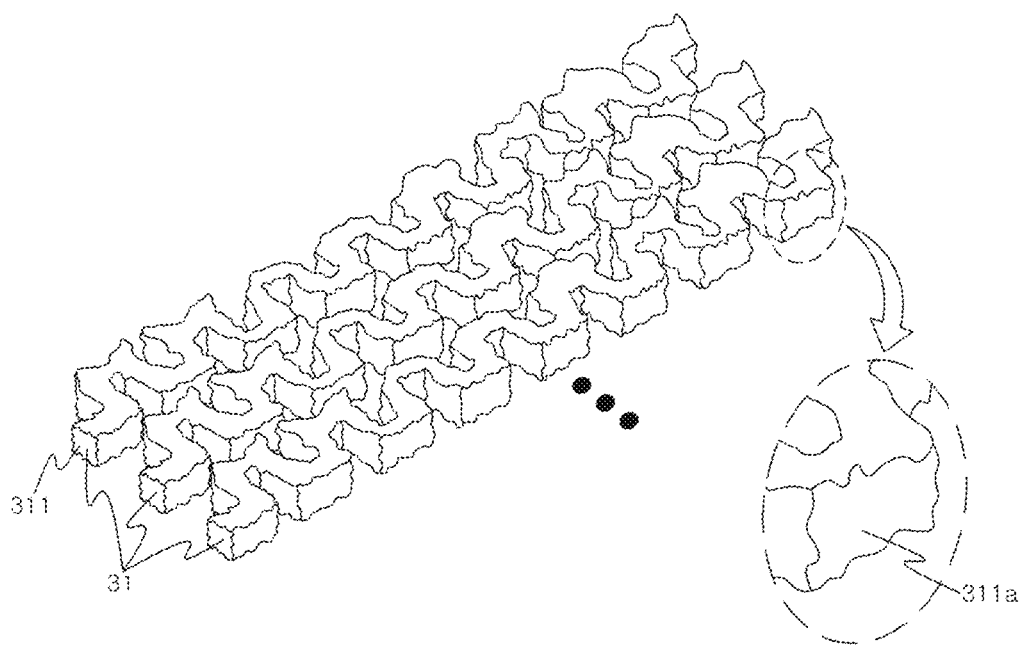
FIG. 7 is a perspective view of porous layers composed of a base layer.

Referring to FIG. 7, the base layer 31 is an assembly of porous layers formed on the surface of the implant 1, and is composed of a plurality of unit base layers 311. No limitations are imposed on the number of unit base layers 311.

The unit base layer 311 is a porous layer that is formed by locally melting the surface of the implant with a laser beam 102 and spraying a metal powder having a predetermined size, preferably a size of 40-150 µm, onto the molten surface. Formed as the metal powder binds to the molten surface of the implant 1, the unit base layer 311 is integrated into the surface of the implant without forming a boundary therebetween. Therefore, a high binding force is provided between the unit base layer 311 and the matrix material of the implant 1 so that they are much less apt to separate from each other even when a shearing load is continuously applied therebetween. Hence, the porous layer made by the method of the present invention can be more reliably used than can that made by the conventional implant surface treating method, TPS (titanium plasma-spray) coating.

Figure 8:
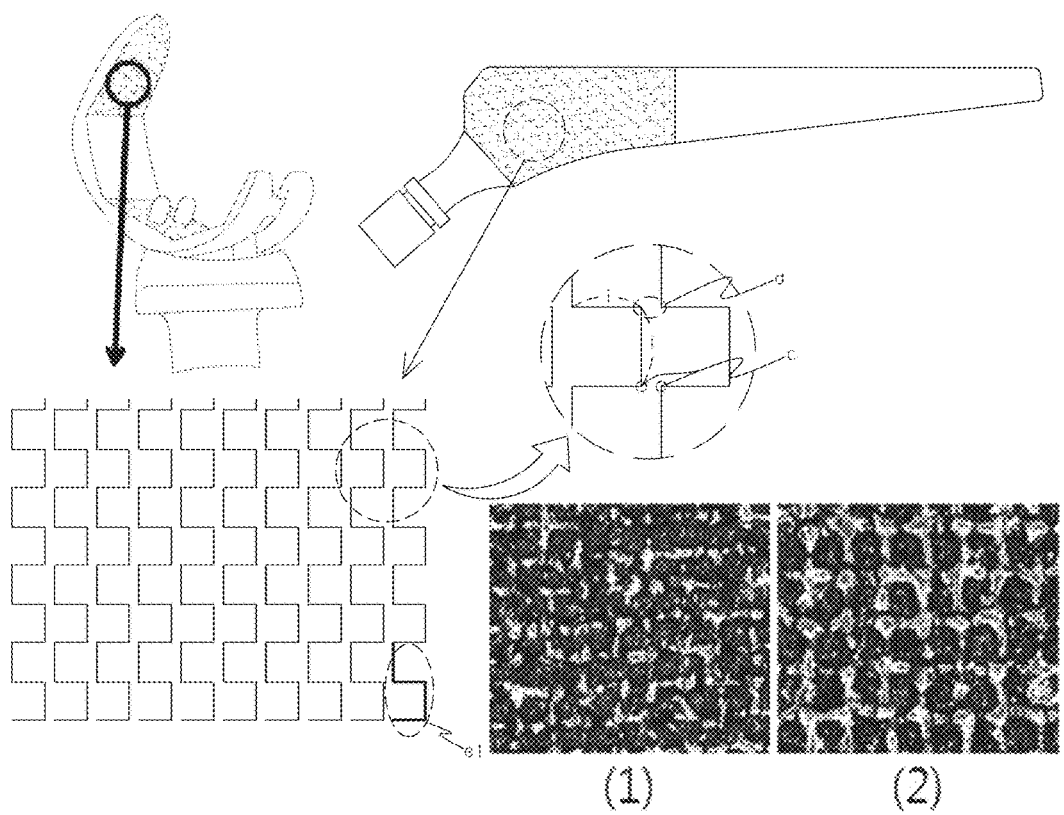
FIG. 8 is a reference view showing an implant whose pore shape and size are adjusted using a moving path of the tool in forming a base layer.

The unit base layer 311 is formed as a first wall 311a is established. For this, a tool that radiates a laser beam 102 and sprays metal powders is repeatedly applied to the surface along a predetermined unit base layer path e1. Referring to FIG. 8, for example, the unit base layer path e1 is set to have a repeating 'right-forward-left-forward' directional pattern. The tool that sprays metal powder and radiates a laser beam 102 is made to move along a repeating pattern so that the first wall 311a is formed in a repeating 'right-forward-left-forward' directional pattern, with the result that the unit base layer 311 is formed. The unit base layer path e1 is the pattern along which the tool moves. The tool may repeatedly move along the unit base layer path e1.

As shown in FIG. 8, the gap between two adjacent unit base layers 311 formed on the surface of the implant matrix material is wide so that the turning point c of one unit base layer 311 is not in contact with that of the other and an interconnecting space d is formed therebetween. Through the interconnecting space d, the pores a in the base layer 31 communicate with each other, thereby increasing the bond adhesion. The turning point c is a corner site at which individual unit base layer paths e1, along which metal powder spraying and laser beam irradiation are conducted to form the wall 311a, rapidly turn. The interconnecting space d is a space formed to allow a valley to pass between adjacent turning points c of neighboring unit base layers 311.

Figure 9:
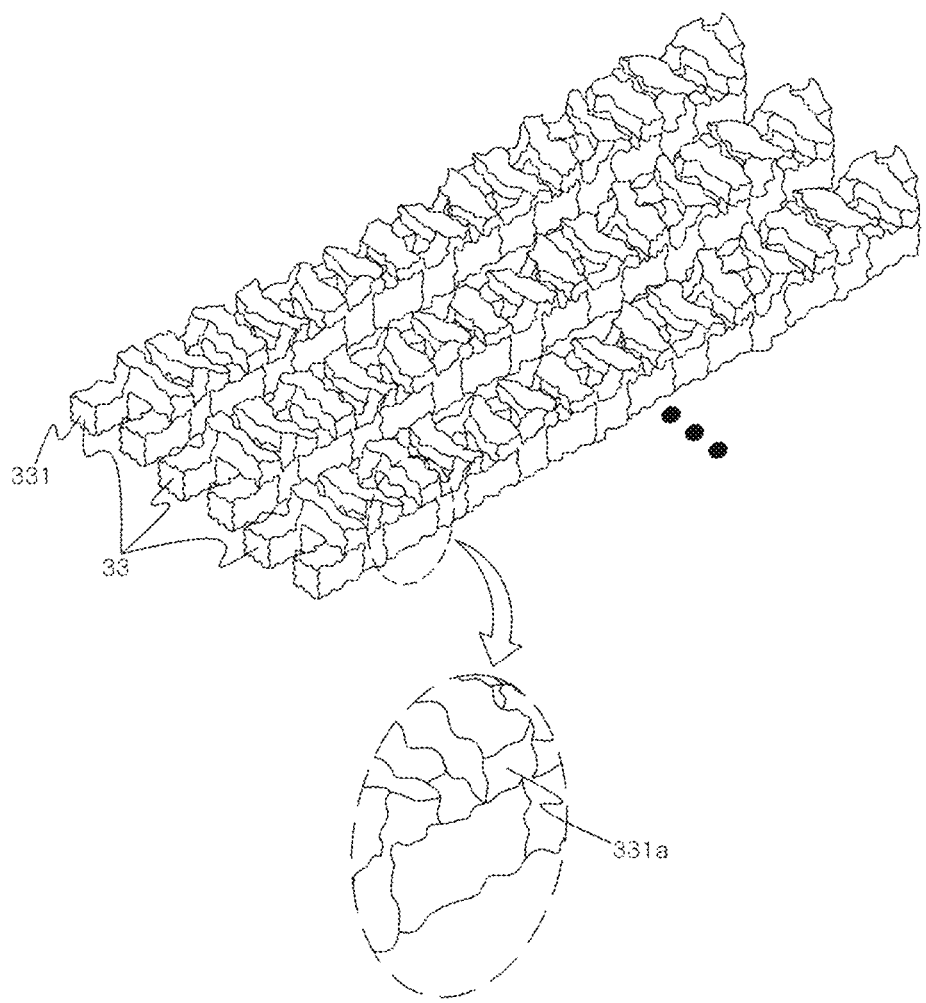
FIG. 9 is a perspective view of porous layers composed of a base layer and an additional layer.

Referring to FIG. 9, the additional layer 33 is an assembly of porous layers, a portion of which are deposited over the base layers 31 by radiating a laser beam 102 and spraying metal powder, with the remainder formed on the surface of the implant. A portion of the additional layer 33 is formed on the upper surface of the base layer 31, increasing the porosity of the porous layer 3. In addition, the formation of the additional layer 33 increases the total height of the porous layer including the base layer 31 and the additional layer 33 deposited on the base layer 31, thus increasing the strength of the implant. Formed in part on the surface of the implant 1, the additional layer 33 increases the roughness of the implant, thus increasing bone adhesion. The additional layer 33 is composed of multiple unit additional layers 331, the number of unit additional layers 331 being identical to the number of unit base layers 311 and varying accordingly.

Figure 10:
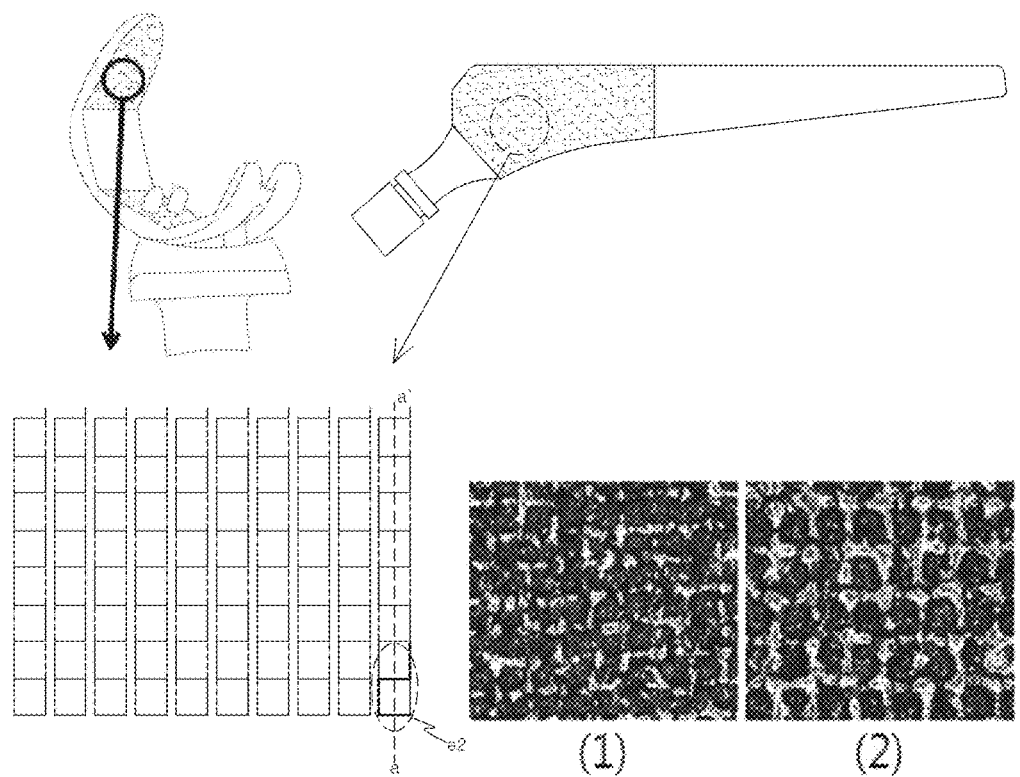
FIG. 10 is a reference view showing an implant whose pore shape and size are adjusted using a moving path of the tool in forming an additional layer.

The unit additional layer 331 is formed by radiating a laser beam 102 along a predetermined unit additional layer path e2 onto the implant 1 and the unit base layer 311 formed on the implant, to melt the upper surface of the unit base layer 311 and the surface of the implant 1, and spraying metal powder having a predetermined size, preferably a size of 40-150 µm, along the irradiation path of the laser beam 102, wherein the metal powder binds to the matrix material of the implant and the upper surface of the unit base layer 311 and is partially deposited on the upper surface of the unit base layer 311, with the remainder formed on the matrix material. The unit additional layer 331 is formed as a second wall 331a is constructed. The construction of the second wall 331a is achieved by forming a deposit portion 331aa on the upper surface of the unit base layer 311 and a sectional portion 331ab on the matrix material. Referring to FIG. 10, for example, after the spraying of metal powder and the irradiation with the laser beam 102 are conducted, along the unit base layer path e1, which is set to have a repeating 'right-forward-left-forward' directional pattern, to form the first wall 311a, the unit additional layer path e2 is set to have a repeating 'left-forward-right-forward' directional pattern symmetrical to the unit base layer path e1 with respect to the a-a' line (hereinafter referred to as the "central line") of the unit base layer, and the spraying of metal powder and the radiation of the laser beam 102 are performed along the unit additional layer path e2 to form the second wall 331a. Here, the tool may first move in a leftward direction to form the unit base layer 311, or may alternatively move first in a right direction to form the unit additional layer 331. Except for the 'forward' direction, the directions set to form the unit base layer 311 may be in the inverse relation with those set to form the unit additional layer 331.

The moving speed of the tool for use in forming the unit base layer 311 and/or the unit additional layer 331 can be adjusted to control the amount of metal powder that is sprayed per unit area and the irradiation time or irradiation intensity of the laser beam 102 per unit area, whereby the unit base layer 311 and/or the unit additional layer 331 including the first wall 311a and/or the second wall 331a can be formed into various shapes according to respective processing conditions. The processing conditions will be described later.

Figure 11:
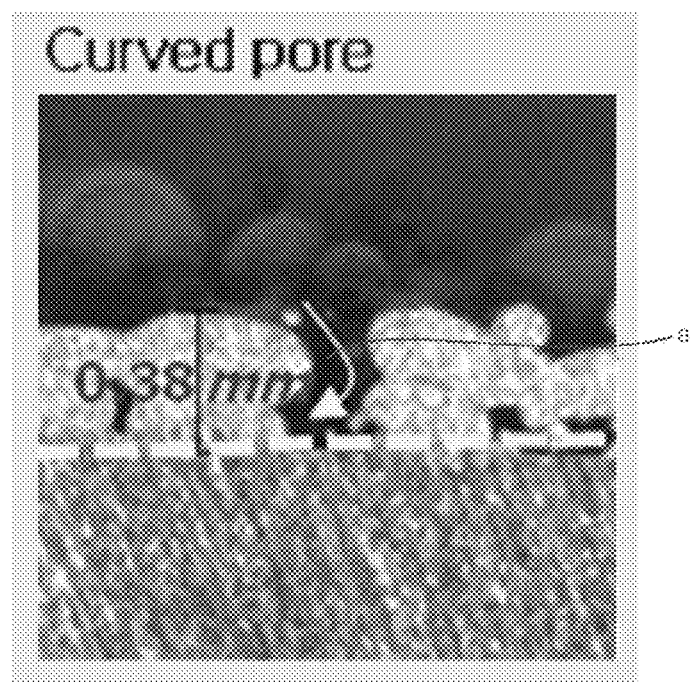
FIG. 11 is an electron microscope image showing the pore shape and thickness of the porous layer of FIG. 3.

When the tool is set to move fast, the amounts of metal powder sprayed over the matrix material at individual turning points c are not very uniform. However, the metal powder is deposited in a relatively uniform amount at slow moving speeds. That is, given a high moving speed, the tool sprays metal powder in non-uniform amounts per unit area to the turning points c to form amorphous pores a. Accordingly, pores a within the unit base layer 311 and/or unit additional layer 331 can be formed in vertically curved shapes through which bones grow to enhance the adhesivity between the bone and the implant. Referring to FIG. 11, for example, the pores through which bone grows into the porous coating layer 3 have a shape that is vertically curved, not vertically straight, with a radius of 100-300 µm, so that the pores allow the bone to grow to the lower end of the curved pores a, thereby increasing the adhesivity between the bone and the implant 1.

Figure 12:
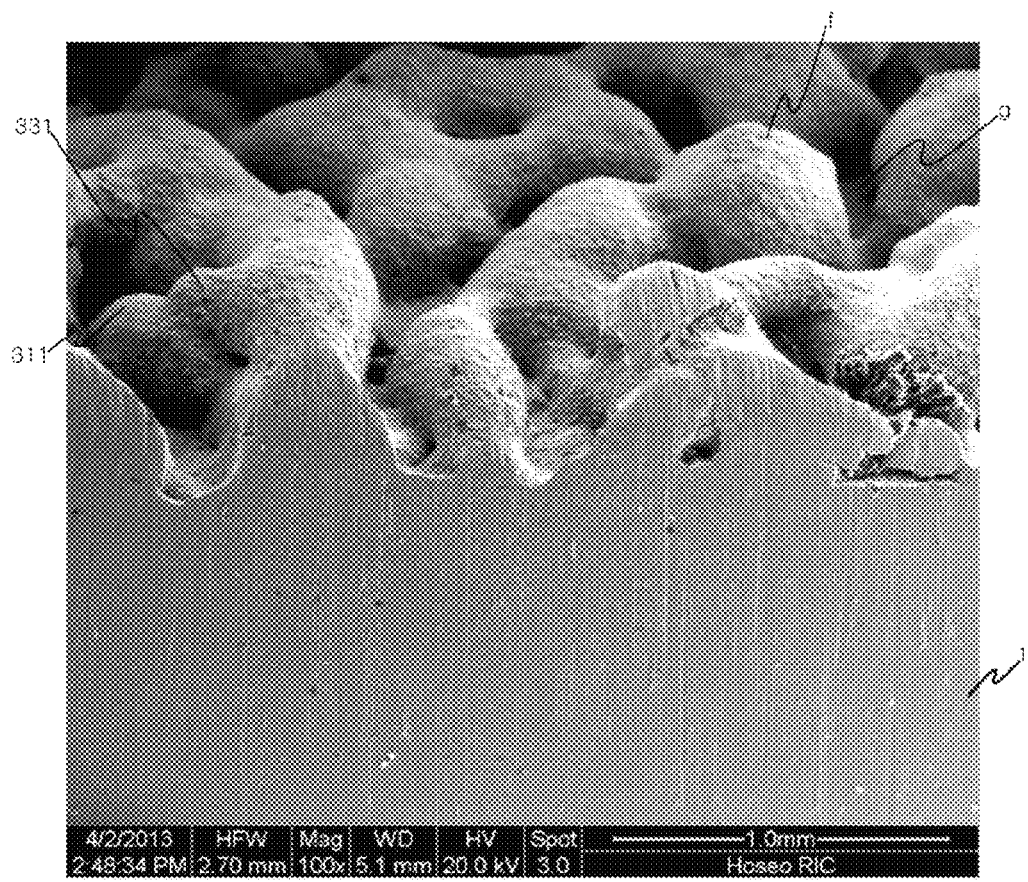
FIG. 12 is an electron microscope image of a porous layer formed on a matrix material surface of the implant.

Turning now to FIG. 12, when the tool is moved fast, as described above, protrusions f and depressions g may be formed in cross-sections of the unit base layer 311 and/or the unit additional layer 331. During the formation of the protrusions f through the melting and solidification of metal powder, bridges h are formed to interconnect protrusions in the same unit base layer 311 and/or the unit additional layer 331. The bone can grow through spaces beneath the bridges, thus connecting pores a with each other and increasing bone adhesion. The protrusion f is a portion that is relatively thick compared to adjacent portions as the first wall 311a and/or the second wall 331a in the unit base layer 311 and/or the unit additional layer 331 are partially interconnected with each other. The depression g is a portion that is relatively thin compared to adjacent portions. As used herein, the term "bridge" refers to a portion that is formed by interconnecting adjacent protrusions d during the solidification of molten metal and beneath which there is a space.

Figure 13:
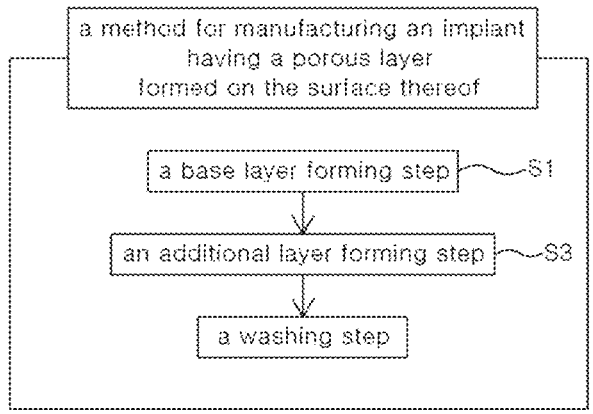
FIG. 13 to FIG. 17 are block diagrams of a method for manufacturing an implant having a porous layer formed on the surface thereof.

Referring to FIG. 13, in accordance with an aspect thereof, the present invention addresses a method for manufacturing an implant having a porous layer formed on the surface thereof, comprising a base layer forming step (S1) in which a base layer 31 is formed on the surface of the implant 1, an additional layer forming step (S3) in which a portion of an additional layer is deposited on the base layer 31, with the remainder formed on the surface of the implant, and a washing step (S5) in which metal powder that remains in a non-molten state is removed from the base layer and the additional layer 33.

Figure 14:
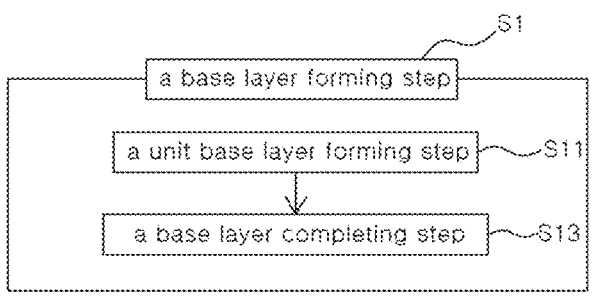
Figure 15:
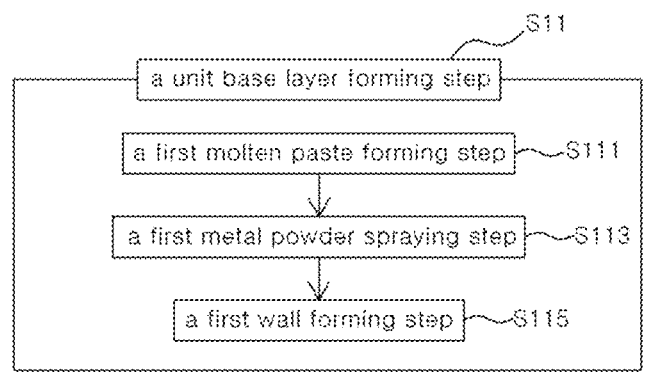

Referring to FIG. 14 and FIG. 15, the base layer forming step (S1) includes: a unit base layer forming step (S11), in which a first wall 311a is constructed on the surface of the implant through a first molten paste forming step (S111), a first metal powder spraying step (S113), and a first wall forming step (S115) to form a unit base layer 311; and a base layer completing step (S13), in which the unit base layer forming step (S11) is repeated to form a base layer 31 composed of multiple unit base layers 311.

In the first molten paste forming step (S111), a laser beam 102 is radiated onto the surface of the implant 1 and locally melts the implant to form a molten paste. Simultaneously, metal powder having a predetermined size, preferably a size of 40-150 μm, is sprayed onto the molten paste in the first metal powder spraying step (S113). The sprayed metal powder is melted, in part by the laser beam 102 and in part by the molten paste.

The first molten paste forming step (S111) and the first metal powder spraying step (S113) are conducted along a predetermined path to form a first wall 311a having a predetermined pattern/thickness/width in the first wall forming step (S115), thereby completing the formation of a unit base layer 311 including the first wall 311a. For example, a unit base layer path e1, along which the irradiation of the laser beam 102 in the first molten paste forming step (S111) and the spraying of metal powder in the metal powder spraying step (S113) are conducted, may be set to be a 'right-forward-left-forward' directional pattern. The radiation of the laser beam 102 and the spraying of metal powder can be repeatedly conducted according to the repeating pattern of the unit base layer path e1. As a result, a unit base layer 311 including the first wall 311a in a repeating 'right-forward-left-forward' pattern can be obtained.

As mentioned above, the tool that functions to spray metal powder and radiate a laser beam 102 is set to move fast, by which the unit base layer 311 including the first wall 311a can be amorphously formed at the turning points c due to the inertia of movement of the tool. For instance, a protrusion f, a depression g and/or a bridge h can be formed to enhance the bone adhesion of the porous layer 3.

Subsequently, the unit base layer forming step (S11) is repeated in the base layer completing step (S13) to complete a base layer 31 composed of multiple unit base layers 311 formed on the implant.

Figure 16:
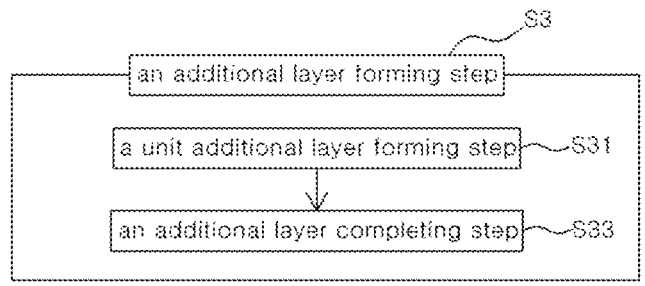
Figure 17:
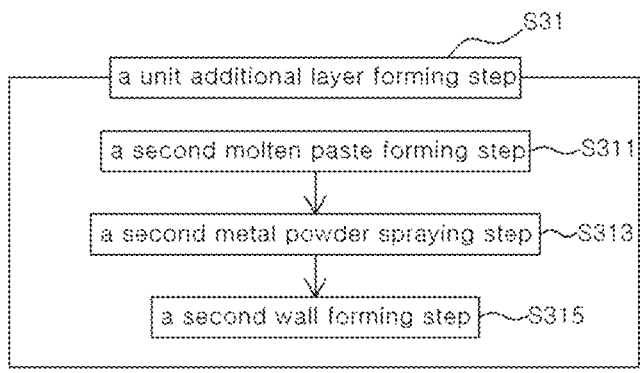

Referring to FIGS. 16 and 17, the additional layer forming step (S3) includes: a unit additional layer forming step (S31), in which a unit additional layer 331 including a second wall 331a is formed through a second molten paste forming step (S311), a second metal powder spraying step (S313), and a second wall forming step (S315); and an additional layer completing step (S33), in which the unit additional layer forming step (S31) is repeated to form an additional layer 33 composed of multiple unit additional layers 331.

In the second molten paste forming step (S311), a laser beam 102 is radiated onto the upper surface of the unit base layer 311 and the surface of the implant 1 to locally form a molten paste. Simultaneously, metal powder with a predetermined size, preferably a size of 40-150 μm, is sprayed onto the molten paste in the second metal powder spraying step (S313).

In the second wall forming step (S315), the second molten paste forming step (S311) and the second metal powder spraying step (S313) are conducted along a predetermined path to form a second wall 331a having a predetermined pattern/thickness/width, thereby completing the formation of a unit additional layer 331 including the second wall 331a. For example, when the unit base layer path e1, along which the radiation of the laser beam 102 and the spraying of metal powder are conducted to form the unit base layer 311, is set to be a 'right-forward-left-forward' directional pattern, a unit additional layer path e2, along which the radiation of the laser beam 102 in the second molten paste forming step (S311) and the spraying of metal powder in the second metal powder spraying step (S313) are conducted, may be set to be a 'left-forward-right-forward' directional pattern, which is symmetric to the unit base layer path e1 for the unit base layer 311 with respect to the central line. In addition, the moving speed of the tool may be adjusted to form protrusions f, depressions g and/or bridges h, as in the unit base layer 311.

In the washing step (S5), metal powder that remains un-molten during the formation of the base layer 31 and the additional layer 33 is removed by washing to increase the porosity due to the empty volumes that the metal powder occupies. For instance, dry ice may be atomized and sprayed at an ultrasonic speed to the surface by dry ice blasting, since dry ice can disappear into air without leaving liquid or solid residues.

Below, the formation of porous layers 3 that are 200-1000 μm thick and have a roughness of 100 μm or higher, with pores 150-800 μm in size formed therein at a porosity of 40-70 vol % is described under various conditions including a moving speed, a movement distance b (a distance from one turning point c to another within the unit base layer and the unit additional layer) of the tool, laser beam intensity, etc.

Test 1—Test for Relationship of Pore Size, Porosity and Roughness of Porous Layer 3 with Process Condition Purpose: Change of pore size, porosity thickness (base layer plus additional layer), and roughness of porous layer 3 with moving speed of tool when a laser output and a tool movement interval were fixed.

Specimen preparation: Various specimens were manufactured under the condition that parameters including the output of laser beam 102, and the movement interval and moving speed of the tool were changed while a path along which metal powder with a size of 40~150 μm was sprayed over a titanium alloy implant and a laser beam 102 moved using a DMT technique was set to be a 'right-forward-left-forward' directional pattern as a unit base layer path e1 upon the formation of the base layer 31 and a 'left-forward-right-forward' directional pattern as a unit additional layer path e2 upon the formation of the additional layer 33.

Herein, the laser output (W) refers to the laser output of the DMT, the tool movement interval refers to a distance from one turning point c to another on the path in the unit base layer and the unit additional layer, and the tool moving speed refers to a speed at which the tool moves while spraying metal powder over the implant 1 and irradiating a laser beam 102 to a target point to form a molten paste.

In the method for manufacturing an implant having a porous layer formed on a surface thereof according to the present invention, the spraying of metal powder over the implant and the irradiation of a laser beam 102 were conducted along the repeated 'right-forward-left-forward' unit base layer path e1 to form a base layer 31. Subsequently, the spraying of metal powder over the implant and the irradiation of a laser beam 102 was again conducted along the repeated 'left-forward-right-forward' unit additional layer path e2 symmetric to the unit base layer path e1 with respect to a central line of the unit base layer 311 to form an additional layer 33, thus completing a porous layer 3.

Test method: The pore size, the porosity, and the layer thicknesses (total thickness of the base layer and the additional layer) were measured according to ASTM F 1854, a stereological test standard for coating layers of the FDA, and the roughness was measured according to ISO 4288, a test standard for roughness of the International Standard Organization (ISO).

Test result: test results are summarized in the following table.

TABLE 1

| Specimen | Laser output (W) | Tool movement interval (mm) | Tool moving speed (m/min) | Pore size (μm), Porosity (%), layer thickness (μm), roughness (μm) |
|---|---|---|---|---|
| 1.1 | 90 | 0.7 | 0.6 | 150~450, 40~65, 800~1000, 280~380 |
| 1.2 | 90 | 0.7 | 1 | 200~500, 50~70, 400~600, 260~360 |
| 1.3 | 90 | 0.7 | 1.4 | 250~550, 55~80, 200~400, 240~340 |
| 2.1 | 100 | 0.7 | 0.8 | 150~450, 40~65, 800~1000, 280~380 |
| 2.2 | 100 | 0.7 | 1.2 | 200~500, 50~70, 400~600, 260~360 |
| 2.3 | 100 | 0.7 | 1.6 | 250~550, 55~80, 200~400, 240~340 |
| 3.1 | 115 | 0.7 | 0.9 | 150~450, 40~65, 800~1000, 280~380 |
| 3.2 | 115 | 0.7 | 1.3 | 200~500, 50~70, 400~600, 260~360 |
| 3.3 | 115 | 0.7 | 1.7 | 250~550, 55~80, 200~400, 240~340 |

When a porous layer was formed on an implant for in vivo insertion in accordance with the present invention, a smaller amount of the metal powder was sprayed per unit area or a smaller amount of the metal powder or matrix material was molten at a faster moving speed, so that the layer was thinner with a larger pore size and porosity. In addition, when the laser beam was irradiated for a shorter period of time due to a faster moving speed of the tool, a thinner layer was formed, with a larger pore size and porosity. Further, a faster moving speed of the tool resulted in smaller roughness.

Test 2—Test for Relationship of Pore Size, Porosity and Roughness of Porous Layer 3 with Process Condition Purpose: Change of pore size, porosity thickness (base layer plus additional layer), and roughness of porous layer 3 with laser output when a tool movement interval and a tool moving speed were fixed.

Specimen preparation: the same as in Test 1.
Test method: the same as in Test 1
Test result: Test results are summarized in Table 2, below.

TABLE 2

| Specimen | Laser output (W) | Tool movement interval (mm) | Tool moving speed (m/min) | Pore size (μm), Porosity (%), layer thickness (μm), roughness (μm) |
|---|---|---|---|---|
| 1.1 | 50 | 0.7 | 0.8 | 250~550, 55~80, 200~400, 240~340 |
| 1.2 | 80 | 0.7 | 0.8 | 200~500, 50~70, 400~600, 260~360 |
| 1.3 | 100 | 0.7 | 0.8 | 150~400, 40~65, 800~1000, 280~380 |
| 2.1 | 80 | 0.7 | 1.2 | 250~550, 55~80, 200~400, 240~340 |
| 2.2 | 100 | 0.7 | 1.2 | 200~500, 50~70, 400~600, 260~360 |
| 2.3 | 1000 | 0.7 | 1.2 | 150~400, 40~65, 800~1000, 280~380 |

When a porous layer was formed on an implant for in vivo insertion in accordance with the present invention, a larger laser output (irradiation intensity) per unit area melt a higher amount of metal powder, resulting in reducing the layer in pore size and porosity, and forming a higher layer thickness and roughness.

It was understood from the data of Tests 1 and 2 that under the condition of a fixed laser output/tool movement interval, a smaller amount of the metal powder was sprayed per unit area at a faster moving speed (a lower irradiation intensity of layer beam 102 per unit area), so that the layer was thinner and provided with larger pore size and porosity. When the irradiation intensity of the laser beam 102 was increased, the pore size and the porosity were reduced while the layer thickness and roughness were increased. In addition, as described above, the amount of metal powder deposited on the implant 1 was relatively non-uniform over the movement path of the tool at a faster moving speed of the tool. On the other hand, the amount was uniform over the movement path at a slower moving speed of the tool. That is, depending on the moving speed of the tool, the amount of metal powder deposited on the implant varied due to the moving inertia of the tool.

Test 3—Test for Relationship of Pore Size, Porosity and Roughness of Porous Layer with Process Condition Purpose: Process condition for the formation of a porous layer having a thickness of 200~1000 μm, a pore size of 150~800 μm, a porosity of 40~70 vol %, and a roughness of 100 μm.

Specimen preparation: the same as in Test 1.
Test method: the same as in Test 1
Test result: Test results are summarized in Table 3, below.

TABLE 3

| Specimen | Laser output (W) | Movement interval (mm) | Moving speed (m/min) | Pore size (μm), Porosity (%), Thickness (μm), Roughness (μm) |
|---|---|---|---|---|
| 1.1 | 90 | 0.5 | 0.6 | 0~150 |
| 1.2 | 100 | 0.5 | 0.8 | 15~40 |
| 1.3 | 115 | 0.5 | 0.9 | 800~1000 |
| 1.4 | 1000 | 0.5 | 1.2 | 180~280 |
| 2.1 | 90 | 0.7 | 0.6 | 150~450 |
| 2.2 | 100 | 0.7 | 0.8 | 40~65 |
| 2.3 | 115 | 0.7 | 0.9 | 800~1000 |
| 2.4 | 1000 | 0.7 | 1.2 | 280~380 |
| 3.1 | 90 | 1 | 0.6 | 450~750 |
| 3.2 | 100 | 1 | 0.8 | 55~80 |
| 3.3 | 115 | 1 | 0.9 | 800~1000 |
| 3.4 | 1000 | 1 | 1.2 | 320~420 |
| 4.1 | 90 | 0.5 | 1 | 50~250 |
| 4.2 | 100 | 0.5 | 1.2 | 25~50 |
| 4.3 | 115 | 0.5 | 1.3 | 400~600 |
| 4.4 | 1000 | 0.5 | 1.5 | 160~260 |
| 5.1 | 90 | 0.7 | 1 | 200~500, 50~70, |
| 5.2 | 100 | 0.7 | 1.2 | 400~600, 260~360 |

TABLE 4

| Specimen | Laser output (W) | Movement interval (mm) | Moving speed (m/min) | Pore size (μm), Porosity (%), Thickness (μm), Roughness (μm) |
|---|---|---|---|---|
| 5.3 | 115 | 0.7 | 1.3 | 200~500, 50~70, |
| 5.4 | 1000 | 0.7 | 1.5 | 400~600, 260~360 |
| 6.1 | 90 | 1 | 1 | 500~800 |
| 6.2 | 100 | 1 | 1.2 | 65~85 |
| 6.3 | 115 | 1 | 1.3 | 400~600 |
| 6.4 | 1000 | 1 | 1.5 | 300~400 |
| 7.1 | 90 | 0.5 | 1.4 | 150~300 |
| 7.2 | 100 | 0.5 | 1.6 | 30~55 |
| 7.3 | 115 | 0.5 | 1.7 | 200~400 |
| 7.4 | 1000 | 0.5 | 1.8 | 100~150 |
| 8.1 | 90 | 0.7 | 1.4 | 250~550 |
| 8.2 | 100 | 0.7 | 1.6 | 55~80 |
| 8.3 | 115 | 0.7 | 1.7 | 200~400 |
| 8.4 | 1000 | 0.7 | 1.8 | 240~340 |
| 9.1 | 90 | 1 | 1.4 | 550~850 |
| 9.2 | 100 | 1 | 1.6 | 70~90 |
| 9.3 | 115 | 1 | 1.7 | 200~400 |
| 9.4 | 1000 | 1 | 1.8 | 280~380 |

As is understood from data of Tables 3 and 4, when the base layer 31 and the additional layer were formed to have a thickness of 200~1000 μm, a pore size of 150~800 μm, a porosity of 40~70 vol %, and a roughness of 100 μm, process conditions were set to include a tool movement interval of 0.5~1.0 mm, a laser output of 90~1000 W, and a tool moving speed of 0.6~2.3 m/min, and preferably a tool movement interval of 0.7 mm, a laser output of 100 W, and a tool moving speed of 1.2 m/min.

Hereinafter, the implant 3 having a porous layer 3 formed a surface thereof in accordance with the present invention is found to have a relatively high porosity of 40~70 vol % and exhibit excellent adhesion strength between the porous layer 3 and the implant 1 and excellent adhesivity between metal powder particles in the porous layer 3, as verified by test data.

Test 4—Test of Tensile Force of an Implant 1 Provided with a Porous Layer 3

Figure 18:
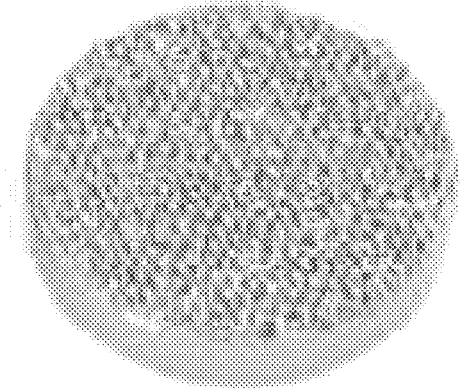
FIG. 18 is an image of a specimen used in Test 4.

Purpose: Measurement of adhesivity or inner cohesion of a porous layer formed on an implant Specimen preparation: Five specimens of FIG. 18, each of which was prepared by applying a porous layer having a thickness (base layer plus additional layer) of 200~1000 μm, a pore size of 150~800 μm and a porosity of 40~70 vol % onto a titanium matrix material having a size of 25.4 mm (diameter)×6.35 mm (height)

Figure 19:
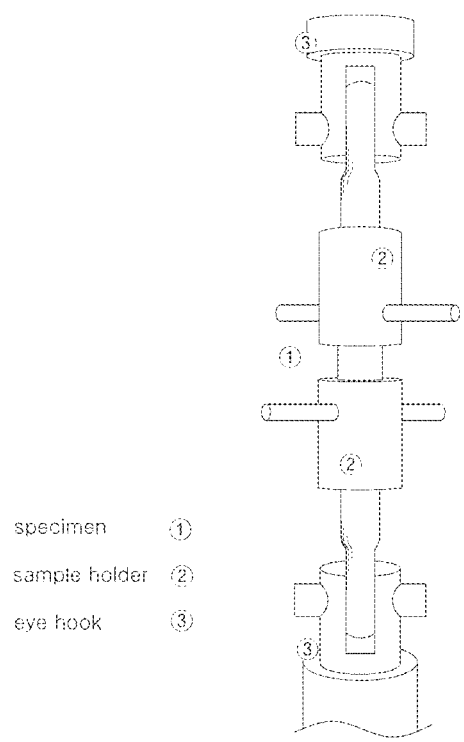
FIG. 19 is an image of a test apparatus used in Test 4.

Test standard: ASTM F 1147, a standard for testing tensile force of a coating layer by the FDA Test method: Test of tensile force was conducted by placing a specimen between upper and lower specimen holders of a tensile force test apparatus (Model No. 360, manufactured by EndoLab Corporation in Germany) shown in FIG. 19 and then applying a tensile load to the specimen at a rate of 2.5 mm/min Test result: Tensile forces of the specimens calculated by the following Equation are given in Table 5, below:

$$\sigma^{tensile}=F/\{(d/2)^2*\pi\}$$

($\sigma^{tensile}$: tensile force, F: applied load, d: size(25.4 mm))

TABLE 5

| Specimen | Maximum load (kN) | Maximum tensile strength (MPa) |
|---|---|---|
| 1.1 | 26.89 | 53.07 |
| 1.2 | 25.95 | 51.22 |

TABLE 5-continued

| Specimen | Maximum load (kN) | Maximum tensile strength (MPa) |
|---|---|---|
| 1.3 | 21.97 | 43.36 |
| 1.4 | 22.65 | 44.71 |
| 1.5 | 25.61 | 50.54 |
| Average | 24.62 | 48.58 |

As apparent from the results of Table 1, the average tensile strength of the implant 1 provided with the porous layer 3 was 48.58 MPa, which exceeds 22 MPa (value determined by the test standard), and none of the specimens underwent the separation of the porous layers.

Test 5—Test for Constant-Volume Shear Force of an Implant 1 Provided with a Porous Layer 1

Purpose: Measurement of adhesivity or inner cohesion of a porous layer formed on an implant Specimen preparation:

Test Example

Figure 20:
FIG. 20 is an image of a specimen used in Test 5.

Five specimens of FIG. 20, each of which was provided with a porous layer having a thickness of 200~1000 μm (base layer plus additional layer), a pore size of 150~800 μm and a porosity of 40~70 vol % onto a titanium matrix material having a size of 19.05 mm (diameter)×25.4 mm (height). The specimens were prepared in the same manner as in Test 1.

Comparative Example

Titanium metal powder was melted and sprayed in a TPS manner over an implant, made of titanium, with a size of 19.05 mm (diameter)×25.4 mm (height) to form a coating layer on a surface of the implant.

Figure 21:
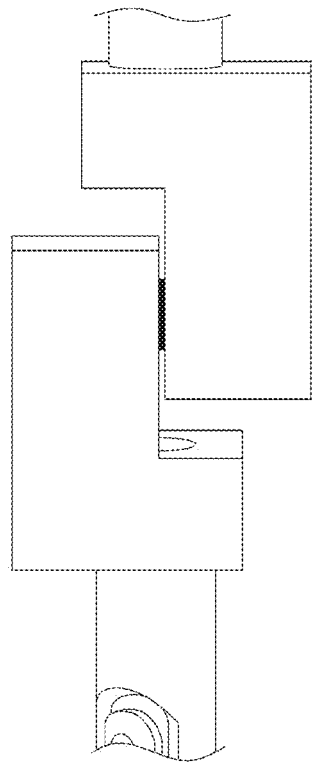
FIG. 21 is an image of a test apparatus used in Test 5.

Test standard: ASTM F 1044, which is the standard for testing shear force of a coating layer by U.S. FDA Test method: Test of shear force was conducted by inserting a specimen between left and right specimen holders of a shear force test apparatus (Model No. 292, manufactured by EndoLab Corporation in Germany) shown in FIG. 21 and then applying a shear load to the specimen at a rate of 2.5 mm/min Test result: Shear forces of the specimens calculated by the following Equation are given in Tables 6 and 7 below:

$$\sigma^{shear}=F/\{(d/2)^2*\pi\}$$

($\sigma^{shear}$: shear force, F: applied load, d: size (19.05 mm))

TABLE 6

| Specimen | Maximum Load (kN) | Max. Tensile Streng (MPa) |
|---|---|---|
| Test Example 1.1 | 13.00 | 45.61 |
| Test Example 1.2 | 13.06 | 45.81 |
| Test Example 1.3 | 14.17 | 49.72 |
| Test Example 1.4 | 12.97 | 45.52 |
| Test Example 1.5 | 12.84 | 45.05 |
| Avg. | 13.21 | 46.34 |

TABLE 7

| Specimen | Maximum Load (kN) | Max. Tensile Streng (MPa) |
|---|---|---|
| Test Example 2.1 | 11.50 | 40.37 |
| Test Example 2.2 | 12.03 | 42.23 |
| Test Example 2.3 | 11.38 | 39.95 |
| Test Example 2.4 | 11.64 | 40.86 |

TABLE 7-continued

| Specimen | Maximum Load (kN) | Max. Tensile Streng (MPa) |
|---|---|---|
| Test Example 2.5 | 12.01 | 42.16 |
| Avg | 11.71 | 41.11 |

Figure 22:
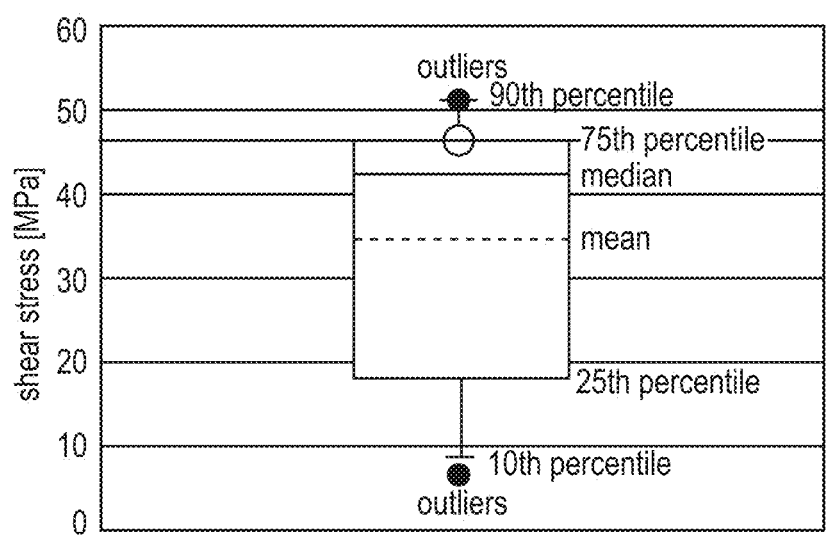
FIG. 22 is a graph showing the position at which the measurement of Test 5 is in statistical data of shear stress.

With reference to FIG. 22, the average shear strength of the implant 1 provided with the porous layer 3 is 46.34 MPa, which exceeds 20 MPa (value determined by the test standard), and none of the specimens underwent the separation of the porous layers. The implant 1 increased in average shear strength by 5.23 MPa, compared to the conventional TPS coating having an average shear strength of 41.11 MPa.

Test 6—Test of Fatigue Shear Force of an Implant 1 Provided with a Porous Layer 3

Purpose: Measurement of shear fatigue and bending fatigue performances of a porous layer formed on an implant Specimen preparation:

Text Example

Figure 23:
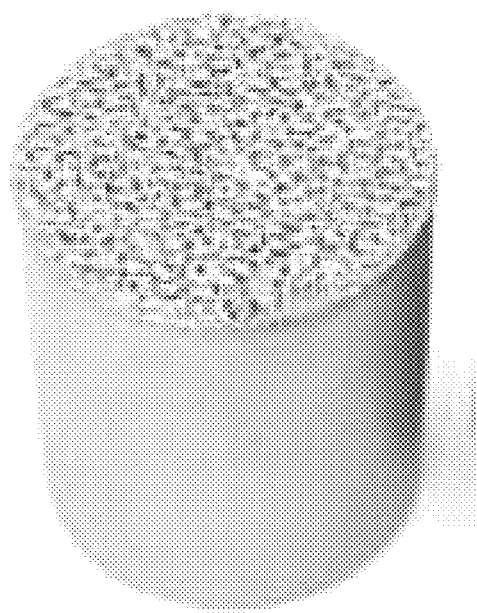
FIG. 23 is an image of a specimen used in Test 6.

Five specimens of FIG. 23, each of which was provided with a porous layer having a thickness of 200~1000 μm (base layer plus additional layer), a pore size of 150~800 μm and a porosity of 40~70 vol % onto a titanium matrix material having a size of 19.05 mm (diameter)×25.4 mm (height). The specimens were prepared in the same manner as in Test 1.

Comparative Example

Titanium metal powder was melted and sprayed in a TPS manner over an implant, made of titanium, with a size of 19.05 mm (diameter)×25.4 mm (height) to form a coating layer on a surface of the implant.

Figure 24:
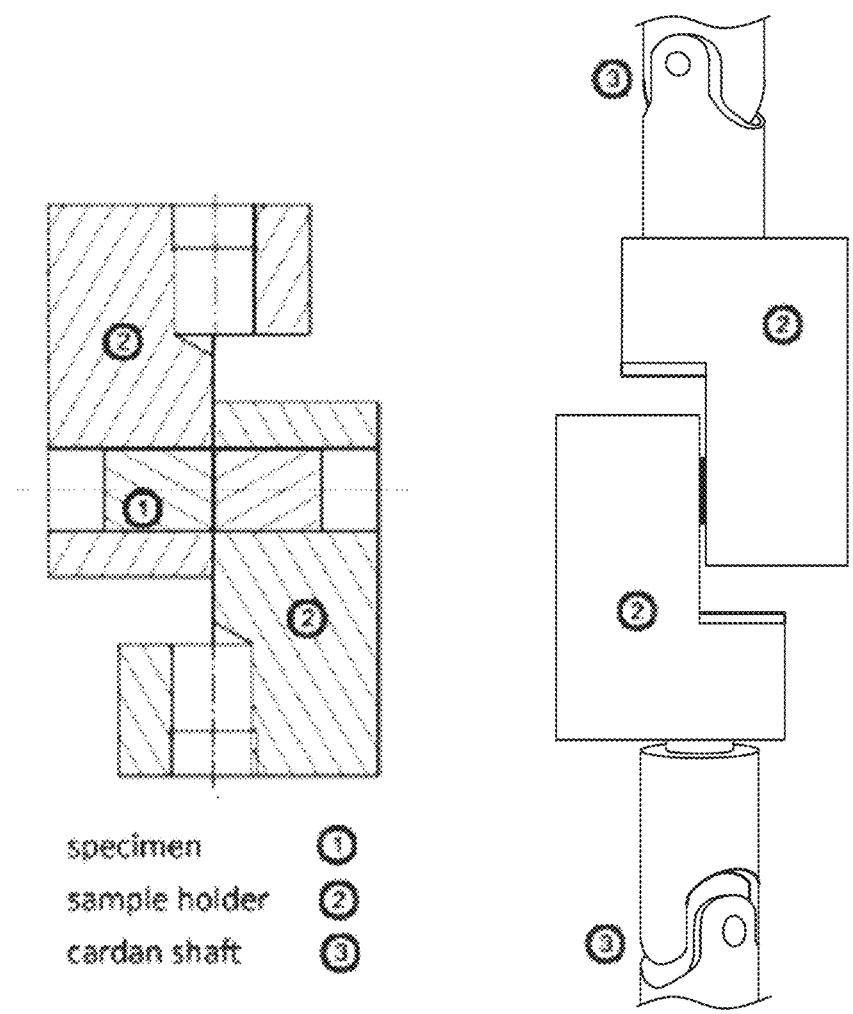
FIG. 24 is an image of a test apparatus used in Test 6.

Test standard: ASTM F 1160, which is the standard for testing shear and bending fatigues of a coating layer by the FDA Test method: Test of shear fatigue and bending fatigue performances was conducted by inserting a specimen between left and right specimen holders of a shear and bending fatigue test apparatus (Model No. 302, manufactured by EndoLab Corporation in Germany) shown in FIG. 24 and then applying a sine-curved dynamic load having a frequency of 20 Hz to the specimen between maximum load and minimum load (minimum load is set to 10% of maximum load) at a cycle (period) of a maximum of ten millions Test result: Shear forces of the specimens calculated by the following Equation are given in Tables 8 and 9 below:

$$\sigma^{shear} = F / \{(d/2)^2 * \pi\}$$

($\sigma^{shear}$: shear force, F: applied load, d: size (19.05 mm))

TABLE 8

| Specimen | Min. load (kN) | Max. load (kN) | Min. shear force (MPa) | Max. shear force (MPa) | Cycle | Fracture |
|---|---|---|---|---|---|---|
| Test Ex. 1.1 | 0.85 | 8.51 | 3.00 | 30.00 | 47,944 | Occurred |
| Test 1.2 | 0.78 | 7.80 | 2.75 | 27.50 | 124,956 | Occurred |
| Test Ex. 1.3 | 0.71 | 7.08 | 2.50 | 24.98 | 535,939 | Occurred |
| Test Ex. 1.4 | 0.64 | 6.38 | 2.25 | 22.50 | 2,298,912 | Occurred |
| Test Ex. 1.5 | 0.50 | 4.96 | 1.75 | 17.50 | 10,000,000 | None |
| Test Ex. 1.6 | 0.57 | 5.67 | 2.00 | 20.00 | 10,000,000 | None |
| Test Ex. 1.7 | 0.57 | 5.67 | 2.00 | 20.00 | 10,000,000 | None |

TABLE 9

| Specimen | Min. load (kN) | Max. load (kN) | Min. shear force (MPa) | Max. shear force (MPa) | Cycle | Fracture |
|---|---|---|---|---|---|---|
| C. Test. Ex 2.1 | 0.85 | 8.51 | 3.00 | 30.00 | 47,944 | Occurred |
| C. Test Ex. 2.2 | 0.78 | 7.80 | 2.75 | 27.50 | 124,956 | Occurred |
| C. Test Ex. 2.3 | 0.71 | 7.08 | 2.50 | 24.98 | 535,939 | Occurred |
| C. Test Ex. 2.4 | 0.64 | 6.38 | 2.25 | 22.50 | 2,298,912 | Occurred |
| C. Test Ex. 2.5 | 0.57 | 5.67 | 2.00 | 20.00 | 10,000,000 | Occurred |
| C. Test Ex. 2.6 | 0.44 | 4.39 | 1.54 | 15.45 | 545.644 | None |
| C. Test Ex.2.7 | 0.44 | 4.39 | 1.54 | 15.45 | 10,000,000 | None |

Figure 25:
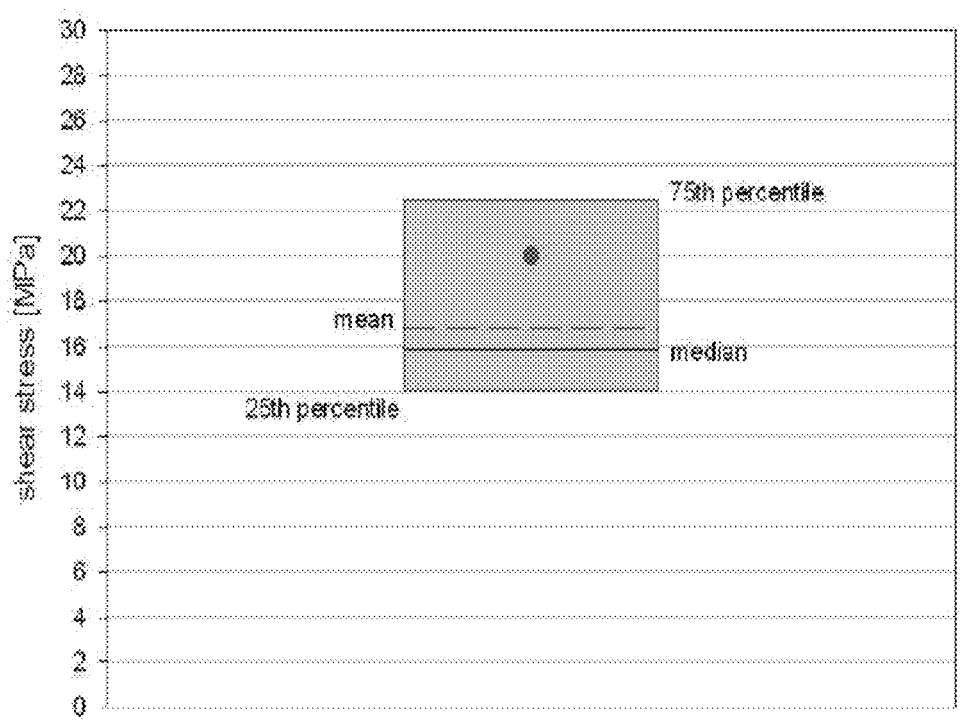
FIG. 25 is a graph showing the position at which the measurement of Test 6 is in statistical data of shear stress.

Even when a dynamic load was applied at a cycle of ten million, the implant (a) provided with the porous layer (b) retained a shear strength of 20.00 MPa and did not undergo fracture, and the porous layer was not detached. Further, the shear strength, as shown in FIG. 25, was found to exceed the average value on statistical data obtained in the same test. Also, the shear strength was increased by 4.55 MPa, compared to a conventional TPS coating, which was measured to retain a shear strength of 15.45 MPa under a dynamic load applied at a cycle of ten million.

Test 7—Test of Wear Resistance of an Implant 1 Provided with a Porous Layer 3

Purpose: Measurement of wear resistance of a coating layer formed on an implant

Figure 26:
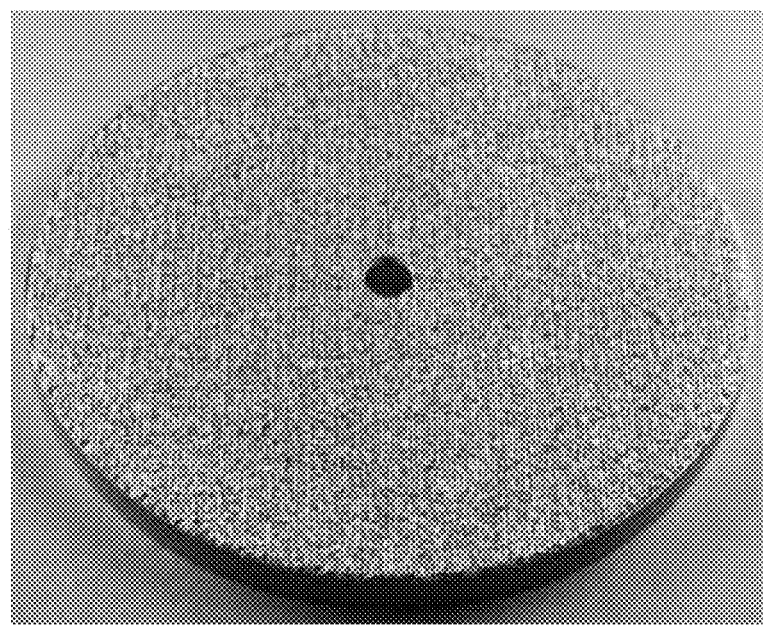
FIG. 26 is an image of a specimen used in Test 7.

Specimen preparation: Six specimens of FIG. 26, each of which was provided with a porous layer having a thickness of 200~1000 μm (base layer plus additional layer), a pore size of 150~800 μm and a porosity of 40~70 vol % onto a titanium matrix material having a size of 100 mm (diameter)×6 mm (height). The specimens were prepared in the same manner as in Test 1.

Figure 27:
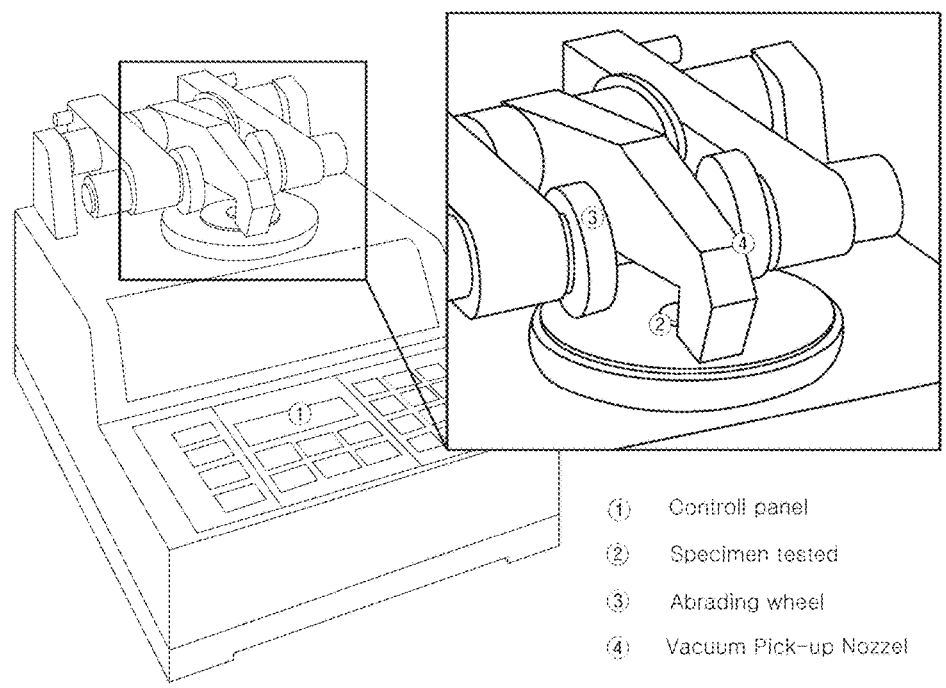
FIG. 27 is an image of a test apparatus used in Test 7.
Figure 28:
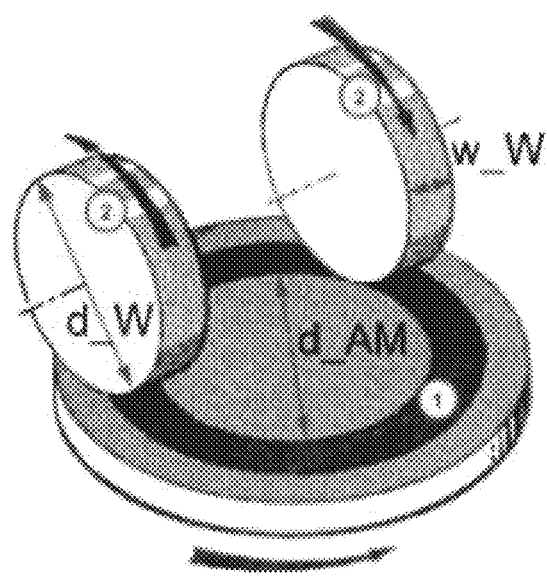
FIG. 28 is a reference view showing the actuation principle of the test apparatus of FIG. 26.

Test standard: ASTM F 1978, which is the standard for testing wear resistance of a coating layer by U.S. FDA Test method: Test of wear resistance was conducted using a wear resistance test apparatus (Model No. 140, 366, manufactured by EndoLab Corporation in Germany) shown in FIG. 27. As shown in FIG. 28, two abrading wheels rotated in a direction opposite to each other by the rotation of a disk on which a specimen is disposed comes into contact with the specimen disposed on the disk, and, at this time, the degree of the specimen being worn is measured. Specifically, test method is conducted by the following steps of: ① measuring the initial weight of a specimen before the test; ② cleaning the specimen and then disposing the cleaned specimen on a disk of the wear resistance test apparatus; ③ bringing the specimen disposed on the disk into contact with two abrading wheels to abrade the specimen; ④ ultrasonically cleaning the abraded specimen for 30 minutes, drying the ultrasonically-cleaned specimen in an oven at 100° C. for 10 minutes, and then cooling the dried specimen at room temperature; and ⑤ measuring the weight of this specimen three times. These steps of ② to ⑤ are cumulatively performed at a cycle of 5, 10 and 100.

Test result: Weight losses per cycle of the specimens calculated by the following Equation are given in Table 10 below:

$$dw_n = w_0 - w_n$$

(dw$_n$: accumulated weight loss, w$_0$: weight measured during the first three times, w$_n$: average weight measured during three times, $_n$: accumulated cycle number)

TABLE 10

| Cumulative cycle | Specimen | | | | | | |
|---|---|---|---|---|---|---|---|
| | 2.1 Wt. loss (mg) | 2.2 Wt. loss (mg) | 2.3 Wt. loss (mg) | 2.4 Wt. loss (mg) | 2.5 Wt. loss (mg) | 2.6 Wt. loss (mg) | Avg. Wt. loss (mg) |
| 0 | 0.00 | 0.00 | 0.00 | 0.00 | 0.00 | 0.00 | 0.00 |
| 2 | 0.50 | 4.20 | 7.30 | 7.00 | 4.40 | 7.00 | 5.07 |
| 5 | 2.20 | 8.60 | 15.10 | 12.00 | 7.50 | 14.50 | 9.98 |
| 10 | 3.70 | 10.70 | 20.60 | 17.00 | 9.60 | 19.90 | 13.58 |
| 100 | 27.80 | 34.00 | 54.60 | 44.80 | 32.60 | 49.60 | 40.57 |

Taken together, the data obtained above show that when the thickness and pore size and shape of the porous layer 3 of the implant 1 of the present invention are accurately controlled, the porous layer 3 has a relatively high porosity of 40~70 vol %, and simultaneously the adhesion strength between the porous layer 3 and the implant 1 (matrix material) and the adhesivity between powder particles in the porous layer 3 can be maintained high, so the adhesivity between the implant 1 and the bone growing into the pores a of the porous layer 3 increases, and the separation of the porous layer 3 from the implant 1 can be prevented in the procedure of operating a thigh stem to prevent the retardation of bone growth, the reduction of stress dissipation effects and the looseness of the implant 1 inserted in the human body, thereby preventing the failure of operation of the implant 1.

According to the present invention, an implant having a porous layer formed a surface thereof can be manufactured wherein the porous layer is given high porosity to enhance bone adhesion into the pores and to increase binding strength between the implant and the porous layer and between particles within the porous layer.

Formed by simultaneously melding metal powder and a matrix material, the porous layer is integrated into the matrix material without boundaries therebetween, thus enhancing binding strength between the porous layer and the matrix material.

According to the present invention, the porous layer contains pores that have a vertically curved shape with a radius of 100~300 μm, thus allowing a bone to grow into the pores to enhance bone adhesion.

In present invention, an interconnection space is formed between turning points in adjacent unit base layers to increase the ratio of interconnection between pores whereby bones are allowed to grow into the pores to increase bone adhesion.

In the present invention, the amount of metal powder sprayed over the implant varies depending on a path, so that a unit base layer and a unit additional layer vary in shape depending on the path, whereby binding strength between the bone and the implant can be increased.

In the present invention, the irradiation intensity and time of a laser beam for melting metal powder is adjusted to allow a unit base layer and a unit additional layer to be formed in different shape depending on a path, whereby binding strength between the bone and the implant can be increased.

In the present invention, a washing step for removing metal powder is carried out to increase a unit base layer and unit additional layer in porosity.

In the present invention, an additional layer is deposited in part on a base layer and the remainder is formed on a surface of the implant, whereby the porous layer can improve in porosity and roughness.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for manufacturing an implant for in vivo insertion, the implant comprising an implant body comprising at least a portion of an orthopedic implant having a porous layer formed on a matrix material surface thereof, the method comprising a base layer forming step for forming a base layer integrated into the matrix material surface of the implant body and an additional layer forming step for forming an additional layer on the implant body in which the base layer is formed, the base layer forming step including:
   a unit base layer forming step for completing a unit base layer by conducting:
      a first molten paste forming step in which a laser beam is radiated into the matrix material surface of the implant body to locally form a molten paste,
      a first metal powder spraying step in which a metal powder predetermined in size is sprayed by a tool over the molten paste to melt into the molten paste, and
      a first wall forming step in which the first molten paste forming step and the first metal powder spraying step are carried out along a first predetermined path to form a first wall having one or more turning points and a predetermined pattern/thickness/width integrated into the surface of the implant body without forming a boundary therebetween; and
   a base layer completing step for completing a base layer composed of multiple unit base layers by repeating the unit base layer forming step, the base layer at least partially forming the porous layer on the matrix material surface of the implant body; and
   the additional layer forming step including:
   a unit additional layer forming step for completing a unit additional layer by conducting:
      a second molten paste forming step in which a laser beam is radiated to an upper surface of the unit base layer and a surface of the implant body to locally form a molten paste;
      a second metal powder spraying step in which metal powder having a predetermined size is sprayed by the tool over the molten paste in the second metal powder spraying step;
      a second wall forming step in which the second molten paste forming step and the second metal powder spraying step are carried out along a second predetermined path to form a second wall having a predetermined pattern/thickness/width; and
   an additional layer completing step for completing an additional layer composed of multiple unit additional base layers by repeating the unit base layer forming step,
   wherein during the first metal powder spraying step the tool is moved at a speed that causes an inertia of the tool to cause non-uniform spraying of powder per unit area over the molten paste at the turning point of at least one of the multiple unit base layers in the first wall forming step, thus causing the first wall to be amorphously formed so that the unit base layer includes one or more depressions, one or more protrusions, and one or more bridges interconnecting adjacent protrusions, wherein the depressions, protrusions, and bridges form pores of empty spaces there between.

2. The method of claim 1, wherein an amount of the metal powder, sprayed over the molten paste, that is molten is controlled by adjusting laser beam irradiation in intensity and/or time per unit area on the path in the first wall forming step when the implant body is locally melted on the surface thereof.

3. The method of claim 1, wherein the base layer formed in the base layer completing step has a predetermined gap between two adjacent unit base layers.

4. The method of claim 3, wherein the gap between the unit base layers formed in the base layer completing step is wide so that a turning point of one of the multiple unit base layers is not in contact with that of a remaining one of the multiple unit base layers, whereby an interconnecting space is formed through which pores in the multiple unit base layers communicate with one another.

5. The method of claim 4, wherein the predetermined path along which the first molten paste forming step and the first metal powder spraying step are carried out in the first wall forming step is composed of a plurality of identical unit base layer paths.

6. The method of claim 1, wherein the additional layer formed in the additional layer completing step has a predetermined gap between two adjacent ones of the unit additional layers.

7. The method of claim 6, wherein the gap between the unit additional layers formed in the additional layer completing step is wide so that a turning point of one unit additional layer is not in contact with that of the other.

8. The method of claim 7, wherein the predetermined path along which the second molten paste forming step and the second metal powder spraying step are carried out in the second wall forming step is composed of a plurality of identical unit additional layer paths.

9. The method of claim 8, wherein the metal powder is sprayed in non-uniform amounts per unit area over the molten paste formed on the upper surface of the base layer and the surface of the implant body at individual turning points in the second wall forming step.

10. The method of claim 9, wherein a molten amount of the metal powder sprayed over the molten paste is controlled by adjusting laser beam irradiation in intensity and/or time per unit area on the path in the first wall forming step when the upper surface of the base layer and the surface of the implant body are locally melted.

11. The method of claim 10, wherein the porous layer formed on the surface of the implant body and/or the upper surface of the base layer has contains pores that are vertically curved, with a radius of 100-300 μm, whereby the pores allow the bone to grow thereinto, thus increasing adhesivity between the bone and the implant body.

12. The method of claim 11, wherein the unit base layers or unit additional layers have protrusions wherein adjacent protrusions are connected to form a bridge beneath which a void exists, allowing a bone to grow therein, so that the pores are interconnected to enhance bone adhesion.

13. The method of claim 12, wherein the tool that radiates the laser beam and sprays metal powder is set to move at a speed of 0.6-2.3 m/min with a movement interval of 0.5-1.0 mm and to produce the laser beam at an intensity of 90-1000 W in the base forming step and the additional layer forming step so that the porous layer formed on the surface of the implant body has a thickness of 200-1000 μm, a pore size of 150-800 μm, a porosity of 40-70 vol %, and a roughness of 100 μm or higher.

14. The method of claim 13, wherein the spraying of the metal powder and the radiation of the laser beam in the first metal powder spraying step and the first molten paste forming step are repeatedly conducted along a unit base layer path set to be a 'right-forward-left-forward' directional pattern.

15. The method of claim 14, wherein the spraying of the metal powder and the irradiation of the laser beam in the second metal powder spraying step and the second molten paste forming step are repeatedly conducted along a unit additional layer path set to be a 'left-forward-right-forward' directional pattern symmetric to the unit base layer path with regard to a central line of the unit base layer.

16. The method of claim 15, wherein the metal powder sprayed to the surface of the implant body in the first metal powder spraying step has a size of 40-150 μm.

17. The method of claim 16, wherein the metal powder sprayed to the surface of the implant body in the second metal powder spraying step has a size of 40-150 μm.

18. The method of claim 17, further comprising a washing step in which metal powder remaining in a non-molten state upon the formation of the base layer or the additional layer is removed by washing after the completion of the additional layer.

19. The method of claim 1, wherein the implant body comprises at least a portion of an artificial knee joint or an artificial hip joint.

20. The method of claim 19, wherein the at least a portion of the artificial knee joint or the artificial hip joint comprises a thigh stem or a hipbone cap of the artificial hip joint.

21. The method of claim 19, wherein the at least a portion of the artificial knee joint or the artificial hip joint comprises a shinbone bonding member or thighbone bonding member of the artificial knee joint.

22. The method of claim 1, wherein the multiple unit base layers forming the base layer comprise a plurality of the walls formed directly on the matrix material surface of the implant body, the plurality of walls being laterally spaced apart so that a gap is formed between adjacent walls along a length of the adjacent walls.

23. The method of claim 22, wherein each of the plurality of walls have an identical structure.

24. The method of claim 1, wherein the speed of the tool is at least 0.6 meters per minute.

25. The method of claim 1, wherein the speed of the tool is at least 1 meter per minute.

26. The method of claim 1, wherein the speed of the tool is between about 0.8 and 1.2 meters per minute.

* * * * *